(12) United States Patent
Watanabe et al.

(10) Patent No.: US 9,076,738 B2
(45) Date of Patent: Jul. 7, 2015

(54) COMPOSITION FOR RESIST UNDERLAYER FILM, PROCESS FOR FORMING RESIST UNDERLAYER FILM, PATTERNING PROCESS, AND FULLERENE DERIVATIVE

(75) Inventors: Takeru Watanabe, Jyoetsu (JP);
Toshihiko Fujii, Jyoetsu (JP); Takeshi Kinsho, Jyoetsu (JP); Tsutomu Ogihara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 754 days.

(21) Appl. No.: 13/183,175

(22) Filed: Jul. 14, 2011

(65) Prior Publication Data

US 2012/0045900 A1 Feb. 23, 2012

(30) Foreign Application Priority Data

Aug. 23, 2010 (JP) ................................. 2010-186579

(51) Int. Cl.
*H01L 21/311* (2006.01)
*C07C 69/753* (2006.01)
*G03F 7/11* (2006.01)
*H01L 21/027* (2006.01)

(52) U.S. Cl.
CPC ........ *H01L 21/31144* (2013.01); *C07C 69/753* (2013.01); *C07C 2104/00* (2013.01); *G03F 7/11* (2013.01); *H01L 21/0271* (2013.01); *H01L 21/31116* (2013.01)

(58) Field of Classification Search
None
See application file for complete search history.

(56) References Cited

U.S. PATENT DOCUMENTS

| 6,528,231 | B1 * | 3/2003 | Tajima et al. ............... 430/270.1 |
| 8,835,092 | B2 * | 9/2014 | Watanabe et al. .......... 430/270.1 |
| 2002/0106909 | A1 | 8/2002 | Kato et al. |
| 2005/0255712 | A1 | 11/2005 | Kato et al. |
| 2009/0274978 | A1 | 11/2009 | Ohashi et al. |

(Continued)

FOREIGN PATENT DOCUMENTS

| JP | A-06-061138 | 3/1994 |
| JP | A-2002-334869 | 11/2002 |

(Continued)

OTHER PUBLICATIONS

Abe et al., "Sub-55-nm Etch Proces Using Stacked-Mask Process," *2005 Dry Process International Symposium*, 2005, pp. 11-12.

(Continued)

*Primary Examiner* — Fernando L Toledo
*Assistant Examiner* — Valerie N Newton
(74) *Attorney, Agent, or Firm* — Oliff PLC

(57) ABSTRACT

The invention provides a composition for a resist underlayer film, the composition for a resist underlayer film to form a resist underlayer film of a multilayer resist film used in lithography, wherein the composition comprises at least (A) a fullerene derivative that is a reaction product of a substance having a fullerene skeleton with a 1,3-diene compound derivative having an electron-withdrawing group and (B) an organic solvent. There can be a composition for a resist underlayer film for a multilayer resist film used in lithography, the composition giving a resist underlayer film having excellent high dry etching resistance, capable of suppressing wiggling during substrate etching with high effectiveness, and capable of avoiding a poisoning problem in upperlayer patterning that uses a chemical amplification resist; a process for forming a resist underlayer film; a patterning process; and a fullerene derivative.

33 Claims, 1 Drawing Sheet

(56) References Cited

U.S. PATENT DOCUMENTS

| | | | |
|---|---|---|---|
| 2010/0035181 A1* | 2/2010 | Sakaguchi et al. | 430/271.1 |
| 2010/0081082 A1* | 4/2010 | Yoshimura et al. | 430/270.1 |
| 2012/0004476 A1* | 1/2012 | Yoon et al. | 585/26 |

FOREIGN PATENT DOCUMENTS

| | | |
|---|---|---|
| JP | A-2004-205685 | 7/2004 |
| JP | A-2004-264710 | 9/2004 |
| JP | A-2006-227391 | 8/2006 |
| JP | A-2007-199653 | 8/2007 |
| JP | A-2009-269953 | 11/2009 |
| WO | WO 2004/066377 A1 | 8/2004 |
| WO | WO 2008/062888 A1 | 5/2008 |

OTHER PUBLICATIONS

Seino et al., "Sub-45nm Resist Process Using Stacked-Mask Process," *Proc. of SPIE*, vol. 6923, 2008, pp. 69232O-1-69232O-8.

Ohno et al., "An Efficient Functionalization of [60]Fullerene. Diels-Alder Reaction Using 1,3-Butadienes Substituted with Electron-Withdrawing and Electron-Donating (Silyloxy) Groups," *Tetrahedron*, vol. 52, No. 14, 1996, pp. 4983-4994.

Johnson, Donald W., "Thermolysis of Positive Photoresists," *SPIE* vol. 469 *Advances in Resist Technology*, 1984, pp. 72-79.

Greene et al., Protective Groups in Organic Synthesis, Third Edition, Wiley-Interscience, 1999, pp. 372-381.

Liou et al., "Diels-Alder Reaction of [60]Fullerene With Dienes Having an Ester Substituent At 1-Position," *Fullerene Science and Technology*, vol. 6, No. 2, pp. 351-359, 1998.

Liu et al., "Synthesis, Characterization, and Intramolecular Diels-Alder Reaction Tandem Dehydroaromatization of a Diene-Diyne," *Chemistry Letters*, vol. 34, No. 7, pp. 938-939, 2005.

Japanese Office Action issued in Application No. 2010-186579; Dated Dec. 25, 2012 (With Partial Translation).

* cited by examiner

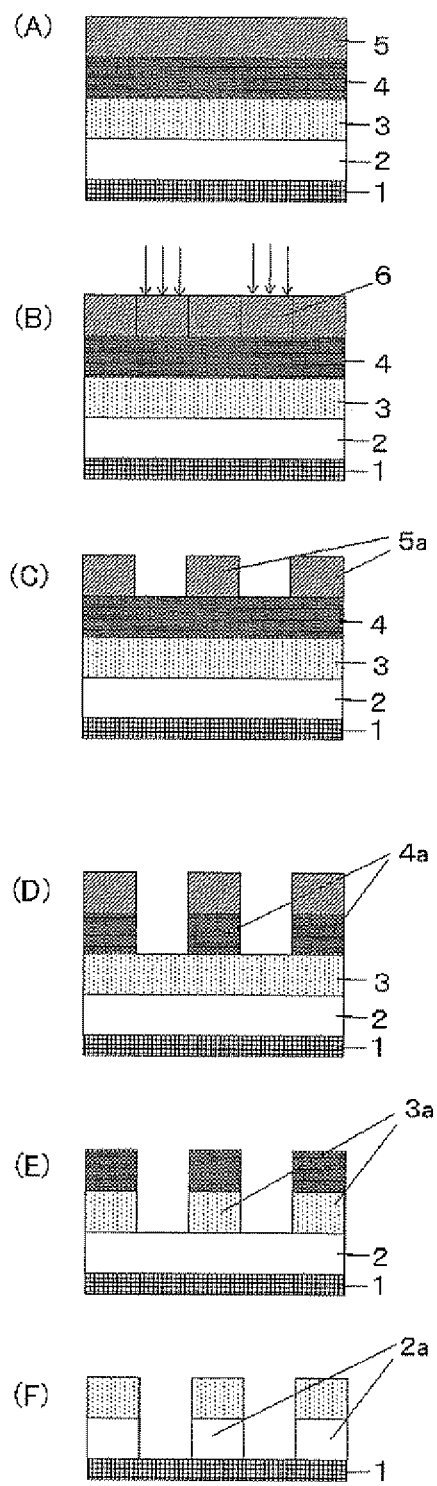

COMPOSITION FOR RESIST UNDERLAYER FILM, PROCESS FOR FORMING RESIST UNDERLAYER FILM, PATTERNING PROCESS, AND FULLERENE DERIVATIVE

BACKGROUND OF THE INVENTION

1. Field of the Invention

The present invention relates to a composition for a resist underlayer film effective for a multilayer resist process used for microfabrication in a process for manufacturing semiconductor devices and the like, a process for forming a resist underlayer film using the same, a resist patterning process using the underlayer film composition suitable for exposure by deep ultraviolet ray, KrF excimer laser light (248 nm), ArF excimer laser light (193 nm), $F_2$ laser light (157 nm), $Kr_2$ laser light (146 nm), $Ar_2$ laser light (126 nm), soft X ray (EUV), an electron beam (EB), an ion beam, X ray and the like, and a fullerene derivative useful in these technical fields.

2. Description of the Related Art

As higher integration and higher speed of LSI are realized, finer pattern size is achieved rapidly. Along with the achievement of finer pattern size, the lithography techniques have accomplished micropatterning by using light sources with shorter wavelength and properly selecting resist compositions corresponding to the light sources. As for such compositions, positive photoresist composition's used as a monolayer are mainly selected. Each of these monolayer positive photoresist compositions has a skeleton providing an etching resistance against dry etching with chlorine-based gas plasma or fluorine-based gas plasma in the resist resin, and has resist mechanism that an exposed area turns soluble, thereby forming a pattern by dissolving the exposed area and dry etching a substrate to be processed to which the resist composition is applied by using the remained resist pattern as an etching mask.

However, when a pattern is rendered finer, that is, a pattern width is rendered narrower, without changing the thickness of a photoresist film to be used, resolution performance of the photoresist film is deteriorated. In addition, developing the pattern of the photoresist film with a developer causes a pattern collapse because a so-called aspect ratio of the pattern becomes too high. Therefore, the thickness of a photoresist film has been made thinner along with achieving a finer pattern.

On the other hand, for processing a substrate to be processed, a method to process the substrate by dry etching by using a pattern-formed photoresist film as an etching mask is usually used. Actually however, there is no dry etching method capable of providing an absolute etching selectivity between the photoresist film and the substrate to be processed. Therefore, the resist film is also damaged and collapsed during processing the substrate, so that the resist pattern cannot be transferred to the substrate to be processed correctly. Accordingly, as a pattern becomes finer, it has been required that a resist composition has a higher dry etching resistance.

In addition, the use of shorter wavelength exposure radiations has required resins used for photoresist compositions to have low light-absorbance at the wavelength to be used. Accordingly, as the radiation shifts from i-line to KrF and to ArF, the resin shifts from novolac resins to polyhydroxystyrene, and to resins having an aliphatic polycyclic skeleton. Along with this shift, an etching rate of the resin actually becomes higher under the dry etching conditions mentioned above, and recent photoresist compositions having a high resolution tend to have a low etching resistance.

As a result, a substrate to be processed has to be dry etched with a thinner photoresist film having lower etching resistance. The need to provide a material for this process and the process itself has become urgent.

A multilayer resist process is one of solutions for these problems. This method is as follows: an intermediate film having a different etching selectivity from a photoresist film, that is, a resist upperlayer film, is set between the resist upperlayer film and a substrate to be processed to obtain a pattern in the resist upperlayer film; the pattern is transferred to the intermediate film by dry etching by using the upperlayer resist pattern as a dry etching mask; and then the pattern is transferred to the substrate to be processed by dry etching by using the intermediate film as a dry etching mask.

In one example of a two-layer resist process, which is one of the multilayer resist processes, a silicon-containing resin is used for the upperlayer resist composition and an organic resin having a high carbon content such as a novolac resin is used for the underlayer film. The silicon resin has a good etching resistance to a reactive dry etching using oxygen plasma, while it is easily removed by etching using fluorine-based gas plasma. On the other hand, the novolac resin is easily removed by a reactive dry etching using oxygen plasma, while it has a good etching resistance to dry etching using fluorine-based gas plasma or chlorine-based gas plasma. In this example, a novolac resin film as a resist intermediate film is formed on a substrate to be processed and a resist upperlayer film using a silicon-containing resin is formed on the resist intermediate film. Then, a pattern is formed in the silicon-containing resist film by irradiation of an energy beam and sequential aftertreatment such as development; part of the novolac resin, on which the resist pattern is removed, is removed by a reactive dry etching using oxygen plasma by using the pattern-formed silicon-containing resist film as a dry etching mask to transfer the pattern to the novolac film; and thereafter, the pattern can be transferred to the substrate to be processed by etching using fluorine-based gas plasma or chlorine-based gas plasma by using the pattern transferred to the novolac film as a dry etching mask.

In such a pattern transfer by the dry etching, when the etching resistance of the etching mask is sufficient, the transferred pattern having a relatively good profile is obtained. Thus, a problem such as a pattern collapse caused by friction and the like by a developer upon resist development hardly occurs, and a pattern having a relatively high aspect ratio can be obtained. Therefore, for example, when the resist film using the novolac resin has the thickness corresponding to the film thickness of the intermediate film, even in the fine pattern which could not be formed directly because of the pattern collapse upon development due to the aspect ratio, according to the above two-layer resist process, the novolac resin pattern having the sufficient thickness as the dry etching mask for the substrate to be processed is obtained.

The multi-layer resist process further include a three-layer resist process which can be performed by using a typical resist composition used in a monolayer resist process. For example, this method is configured to form: an organic film based on novolac or the like as a resist underlayer film on a substrate to be processed; a silicon-containing film as a resist intermediate film thereon; and a usual organic photoresist film as a resist upperlayer film thereon. Since the organic resist upperlayer film exhibits an excellent etching selectivity ratio relative to the silicon-containing resist intermediate film for dry etching by fluorine-based gas plasma, the resist pattern is transferred to the silicon-containing resist intermediate film by means of dry etching based on fluorine-based gas plasma. According to this process, as well as two-layer resist process, patterns of novolac films having sufficient dry etching resistances for processing can be obtained insofar as patterns can be transferred to silicon-containing films, even by adopting: a resist composition which is difficult to be formed with a pattern having a sufficient film thickness for direct processing of a substrate to be processed; and a resist composition having an insufficient dry etching resistance for processing of a substrate.

While numerous techniques have been known (such as Japanese Patent Laid-Open (kokai) No. 2004-205685 and the like) for the organic underlayer film as described above, accompanying decrease of processing line width, further improvement of dry etching resistance are required. Such problems that phenomena of wiggling, bending, and the like (collectively means wiggling) of a resist underlayer film are caused when the resist underlayer film is used as a mask for etching a substrate to be processed (Proc. of Symp. Dry. Process, (2005), p 11), and these problems are caused notedly especially when a finer pattern of 40 nm or less is formed. Such wiggling of a finer pattern is considered to be caused by swell of the underlayer film due to an increased volume thereof and a lowered glass transition point thereof by a phenomenon having been reported, in which hydrogen atoms of a resist underlayer film are substituted with fluorine atoms during etching of a substrate by a fluorocarbon-based gas (Proc. Of SPIE Vol. 6923, 692320, (2008)). In turn, it has been reported that the problem of wiggling can be prevented by adopting an organic material, which is low in hydrogen atom content ratio, and that the problem of dry etching resistance can be improved by adopting an organic material, which is high in carbon atom content ratio, as a resist underlayer film. In this respect, amorphous carbon films formed by CVD are each allowed to be extremely high in carbon atom content ratio and extremely less in hydrogen atom content ratio in the film itself, and are effective for having excellent dry etching resistance and prevention of wiggling. However, CVD is unfortunately insufficient in filling-up characteristic of a stepped substrate, and it is often difficult to introduce a CVD apparatus due to the problems of its high cost and an increased footprint occupation area of the apparatus. Therefore, it will be able to obtain a remarkable merit of cost reduction by simplification of a process and an apparatus, if the above problem of wiggling is solved based on a resist underlayer film composition which can be formed into a film by coating, particularly by spin coating.

As the above-described film-forming material which is high in carbon atom content ratio and low in hydrogen atom content ratio and which can be coated and formed into a film, films each containing a fullerene derivative having extremely high in carbon ratio have been proposed. For example, a method for forming a film by fullerene itself (here, fullerene is a collective term of allotropes of carbon possessing a closed shell cluster composed of many carbon atoms, is typified by $C_{60}$ and $C_{70}$ and includes $C_{74}$, $C_{76}$, $C_{78}$, $C_{82}$, $C_{84}$, $C_{90}$, $C_{94}$, $C_{99}$, $C_{108}$ and further higher carbon clusters) was proposed at the earliest stage (Japanese Patent Laid-Open (kokai) No. H06-61138), but it was difficult to use fullerene itself because fullerene was extremely poor in solubility in a general solvent coated on a substrate. Accordingly, in Japanese Patent Laid-Open (kokai) No. 2004-264710, Japanese Patent Laid-Open (kokai) No. 2006-227391), for example, fullerene was converted to its derivative soluble in a solvent for application and the fullerene derivative was dispersed into an organic resin to obtain a cured film. However, because of the conversion of a fullerene to its derivative, a problem that the key hydrogen atom containing ratio and carbon atom containing ratio largely change has been caused. To solve that problem, in WO2008/62888, it was proposed to use a fullerene-amine adduct (aminated fullerene), which is a derivative having a possibility of generating a fullerene or a substance having a similar hydrogen atom and carbon atom containing ratio to a fullerene by heat decomposition. This technique is important in respect of maximizing the merit of using the fullerene derivative. On the other hand, in a multilayer resist process, an intermediate layer is formed on an underlayer film as appropriate, and then an upperlayer resist is formed to form a pattern, while a chemically amplified resist acting by acid catalyst reaction is used as the upperlayer resist. Therefore, when an amine base generated by heat decomposition of the fullerene derivative (fullerene-amine adduct) reaches the upper resist film even in minute amounts, it affects the acid catalyst reaction in forming the upper resist pattern to cause a so-called poisoning problem such as deterioration of a pattern profile and a development defect.

SUMMARY OF THE INVENTION

The present invention was made in view of the situation as mentioned above, and has an objective to provide; a composition for a resist underlayer film for a multilayer resist film used in lithography, the composition giving a resist underlayer film having excellent high dry etching resistance, capable of suppressing wiggling during substrate etching with high effectiveness, and capable of avoiding a poisoning problem in upperlayer patterning that uses a chemical amplification resist; a process for forming a resist underlayer film; a patterning process; and a fullerene derivative.

To accomplish the foregoing object, according to the present invention, provided is a composition for a resist underlayer film, the composition for a resist underlayer film to form a resist underlayer film of a multilayer resist film used in lithography, wherein the composition comprises at least (A) a fullerene derivative that is a reaction product of a substance having a fullerene skeleton with a 1,3-diene compound derivative having an electron-withdrawing group and (B) an organic solvent.

When the composition for a resist underlayer film as mentioned above is used, the fullerene derivative (A) is soluble in an organic coating solvent and a derivatized side chain that is necessary to make the derivative soluble in the organic solvent is thermally decomposed, so that substantially carbon density of the underlayer film may be increased while decreasing hydrogen density thereof, and thus giving excellent dry etching resistance and suppressing wiggling during etching with high effectiveness. In addition, a decomposition product of the derivatized side chain of the fullerene derivative (A) is, because of its structure, not a basic compound such as an amine; and thus, a harmful effect to a pattern profile during upperlayer resist patterning can be suppressed.

Here, it is preferable that the fullerene derivative contain "n" numbers of a partial structure shown by the following general formula (1).

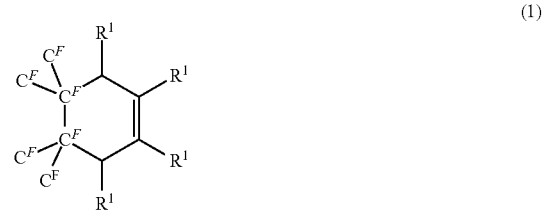

(1)

(Wherein, each $R^1$ independently represents a hydrogen atom, a nitro group, a cyano group, a carboxyl group, a hydroxy group, and a sulfo group; and a monovalent organic group having 1 to 20 carbon atoms which may contain any one or more of a cyano group, a carboxyl group, a hydroxy group, a nitro group, a sulfo group, a carbonyl group, an ether group, an ester group, a sulfone group, and a halogen atom, wherein one or more $R^1$ is an electron-withdrawing group. Two or more $R^1$ may be bonded with each other to form a ring. $C^F$ represents a carbon atom that composes a fullerene skeleton of the fullerene derivative. Reference character "n" represents an integer of 1 to 30.)

As mentioned above, a preferred embodiment of the fullerene derivative (A) contains "n" numbers of the partial structure shown by the general formula (1). $R^1$ in the general formula (1) is effective to secure solubility of the fullerene derivative into a solvent used for an underlayer film. In addition, the partial structure shown by the general formula (1) can be synthesized relatively easily, and in addition, has a role to substantially increase carbon density of the underlayer film and decrease hydrogen density thereof by decomposition during formation of an underlayer film and heat treatment thereof. A decomposition product of the partial structure shown by the general formula (1) is not a basic compound such as an amine so that a harmful effect to a pattern profile during upperlayer resist patterning can be suppressed.

In addition, the electron-withdrawing group is preferably any of a cyano group, a carboxyl group, a nitro group, a sulfo group, an acyl group, an alkoxy carbonyl group, an alkane sulfonyl group, and a trifluoromethyl group.

A usual reaction product of a 1,3-diene compound derivative with a substance having a fullerene skeleton (fullerenes) is poor in its stability near room temperature in some cases; but the stability can be secured when the 1,3-diene compound derivative contains an electron-withdrawing group. On the other hand, decomposition of the product takes place easily during formation of an underlayer film and heat treatment thereof thereby giving fullerenes having high carbon density and low hydrogen density, so that excellent etching resistance and wiggling prevention effect can be obtained. In addition, solubility into a coating solvent and coating properties can be improved as compared with the case that all of $R^1$ in the general formula (1) are hydrogen atoms or hydrocarbon groups.

Further, the 1,3-diene compound derivative having an electron-withdrawing group is preferably a sorbate ester.

Various derivatives of the sorbate ester can be obtained easily and cheaply in industrial production. In addition, the ester has excellent reactivity with fullerenes; and further, the reaction product thereof has excellent solvent solubility and storage stability. The ester can substantially increase carbon density of an underlayer film and decrease hydrogen density thereof as well by decomposition during formation of the underlayer film and heat treatment thereof.

In addition, it is preferable that the fullerene derivative contain "n" numbers of a partial structure shown by the following general formula (1a).

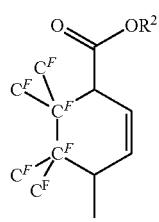

(1a)

(Wherein, $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom. $C^F$ represents a carbon atom that composes a fullerene skeleton of the fullerene derivative. Reference character "n" represents an integer of 1 to 30.)

As mentioned above, when the fullerene derivative is mainly comprised of a substance having "n" numbers of the partial structure shown by the general formula (1a), the fullerene derivative can have excellent solvent solubility and storage stability, and in addition, can substantially increase carbon density of an underlayer film and decrease hydrogen density thereof as well by decomposition during formation of the underlayer film and heat treatment thereof.

Further, it is preferable that the composition for a resist underlayer film contain further (C) a resin having an aromatic ring.

As mentioned above, it is preferable that the composition for a resist underlayer film contain (C) a resin having an aromatic ring, because coating properties at the time of spin coating and filling-up characteristic of stepped substrate can be improved.

Further, it is preferable that (C) the resin having an aromatic ring contain a naphthalene ring.

As mentioned above, it is preferable that (C) the resin having an aromatic ring in the composition for a resist underlayer film contain a naphthalene ring, because etching resistance and optical properties can be improved.

Further, it is preferable that (C) the resin having an aromatic ring contain at least a compound (C1) that is obtained by polycondensation of a compound shown by the following general formula (2) and a compound shown by the following general formula (3) under an acidic condition.

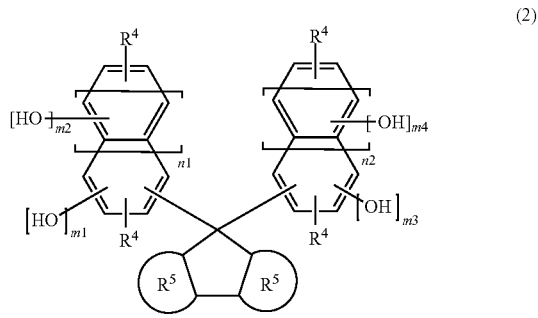

(2)

(Wherein, each $R^4$ independently represents a hydrogen atom or a hydrocarbon group having 6 to 20 carbon atoms; each $R^5$ independently represents a benzene ring or a naphthalene ring; $1 \leq m1+m2 \leq 2$ and $1 \leq m3+m4 \leq 2$; and n1 and n2 are 0 or 1, respectively.)

A-CHO (3)

(Wherein, A represents any of a hydrogen atom, a linear, a branched, or a cyclic saturated or unsaturated hydrocarbon group having 1 to 20 carbon atoms, and an aromatic hydrocarbon group having 6 to 20 carbon atoms, wherein A may contain an ether group, a nitro group, a hydroxy group, or a chlorine group.)

When the composition for a resist underlayer film of the present invention contains (C) a resin having an aromatic ring containing this compound (C1), a resist underlayer film formed therefrom can be made to have excellent filling-up characteristic of stepped substrate and good solvent resistance; and in addition, etching resistance can be improved more effectively, wiggling during substrate etching can be suppressed, and pattern roughness after etching can be made better.

It is preferable that the composition for a resist underlayer film contain further at least one kind selected from the group composed of (D) a phenolic-hydroxy containing compound, (E) an acid generator, (F) a crosslinking agent, and (G) a surfactant.

As mentioned above, to facilitate a crosslinking reaction further, the composition for a resist underlayer film of the present invention may contain (D) a phenolic-hydroxy group containing compound, (E) an acid generator, and (F) a crosslinking agent; and to increase coating properties in spin coating, the composition may contain (G) a surfactant.

In addition, the present invention provides a process for forming a resist underlayer film, the process for forming a resist underlayer film of a multilayer resist film used in lithography, wherein the composition for a resist underlayer film of the present invention is applied onto a substrate and then the composition for a resist underlayer film is cured by heat-treatment at a temperature of 200° C. or higher and 600° C. or lower and a time of 10 to 600 seconds to form a resist underlayer film.

As mentioned above, when the composition for a resist underlayer film of the present invention is applied for coating and then the composition for a resist underlayer film is cured by heat-treatment at a temperature of 200° C. or higher and 600° C. or lower and a time of 10 to 600 seconds, a crosslinking reaction is facilitated so that a mixing with a resist upperlayer film and a resist intermediate film can be avoided. In addition, in the fullerene derivative (A) in the composition for a resist underlayer film of the present invention, the derivatized side chain is partially decomposed during formation of an underlayer film, so that excellent etching resistance can be obtained and at the same time wiggling during etching can be suppressed with high effectiveness.

In addition, the present invention provides a process for forming a resist underlayer film, the process for forming a resist underlayer film of a multilayer resist film used in lithography, wherein the composition for a resist underlayer film of the present invention is applied onto a substrate and then the composition for a resist underlayer film is cured by baking under an atmosphere of oxygen concentration of 0.1% or higher and 21% or lower to form a resist underlayer film.

When the composition for a resist underlayer film of the present invention is baked under the oxygen atmosphere as mentioned above, an adequately cured resist underlayer film can be obtained.

In addition, the present invention provides a patterning process, the patterning process to form a pattern on a substrate by lithography, wherein the process comprises at least:
a step of forming a resist underlayer film on a substrate by using the composition for a resist underlayer film of the present invention,
a step of forming, over the resist underlayer film, a resist intermediate film by using a silicon-containing composition for a resist intermediate film,
a step of forming, over the resist intermediate film, a resist upperlayer film by using a composition for a resist upperlayer film comprised of a photo resist composition thereby forming a multilayer resist film,
a step of forming a resist pattern of the resist upperlayer film by developing with a developer after a pattern circuit area of the resist upperlayer film is exposed,
a step of etching the resist intermediate film by using a mask of the resist upperlayer film formed with the pattern,
a step of etching the resist underlayer film by using a mask of the resist intermediate film at least formed with a pattern, and
a step of etching the substrate by using a mask of the resist underlayer film at least formed with a pattern thereby forming a pattern on the substrate.

When the patterning process like this three-layer resist process is used, a fine pattern can be formed on a substrate with high precision; and thus, the composition for an underlayer film of the present invention is suitable as the composition for an underlayer film for such process.

Etching of the resist underlayer film by using a mask of the resist intermediate layer can be carried out in an etching gas mainly comprised of an oxygen gas or a hydrogen gas.

The silicon-containing resist intermediate film has etching resistance against etching with oxygen gas or a hydrogen gas; and thus, etching of the resist underlayer film by using a mask of the resist intermediate layer can be carried out in an etching gas mainly comprised of an oxygen gas or a hydrogen gas.

In addition, the present invention provides a patterning process, the patterning process to form a pattern on a substrate by lithography, wherein the process comprises at least:
a step of forming a resist underlayer film on a substrate by using the composition for a resist underlayer film of the present invention,
a step of forming, over the resist underlayer film, an inorganic hard mask intermediate film selected from a silicon oxide film, a silicon nitride film, and a silicon oxynitride film,
a step of forming, over the inorganic hard mask intermediate film, a resist upperlayer film by using a composition for a resist upperlayer film comprised of a photo resist composition,
a step of forming a resist pattern of the resist upperlayer film by developing with a developer after a pattern circuit area of the resist upperlayer film is exposed,
a step of etching the inorganic hard mask intermediate film by using the obtained resist pattern as an etching mask,
a step of etching the resist underlayer film by using the obtained inorganic hard mask intermediate film pattern as an etching mask, and
a step of etching the substrate by using the obtained resist underlayer film pattern as an etching mask thereby forming a pattern on the substrate.

In addition, the present invention provides a patterning process, the patterning process to form a pattern on a substrate by lithography, wherein the process comprises at least:
a step of forming a resist underlayer film on a substrate by using the composition for a resist underlayer film of the present invention,
a step of forming, over the resist underlayer film, an inorganic hard mask intermediate film selected from a silicon oxide film, a silicon nitride film, and a silicon oxynitride film,
a step of forming, over the inorganic hard mask intermediate film, an organic anti-reflective film,
a step of forming, over the organic anti-reflective film, a resist upperlayer film by using a composition for a resist upperlayer film comprised of a photo resist composition,
a step of forming a resist pattern of the resist upperlayer film by developing with a developer after a pattern circuit area of the resist upperlayer film is exposed,
a step of etching the organic anti-reflective film and the inorganic hard mask intermediate film by using the obtained resist pattern as an etching mask, a step of etching the resist underlayer film by using the obtained inorganic hard mask intermediate film pattern as an etching mask, and a step of etching the substrate by using the obtained resist underlayer film pattern as an etching mask to form a pattern on the substrate.

In these patterning processes, the composition for a resist underlayer film of the present invention is effective. A photo resist film may be formed as the resist underlayer film on the resist intermediate film, but it may also be possible to form a photo resist film on an organic anti-reflective film (BARC) that is formed by spin coating on the resist intermediate film. When a SiON film (silicon oxynitride film) is used as the resist intermediate film, reflection can be suppressed even in an immersion exposure with high NA beyond 1.0 by virtue of two anti-reflective films of the SiON film and the BARC film. Another merit of forming BARC resides in that it has an effect to reduce a footing profile of a photo resist pattern immediately above SiON.

In this case, it is preferable that the inorganic hard mask intermediate film be formed by a CVD method or an ALD method.

The resist underlayer film used in the present invention has high heat resistance so that it can endure high temperature of 300 to 500° C.; and thus, a combination of an inorganic hard mask formed by a CVD method or an ALD method with a resist underlayer film formed by spin coating is possible.

In addition, the present invention provides a fullerene derivative that is a reaction product of a substance having a fullerene skeleton with a sorbate ester.

A fullerene derivative that is a reaction product of a substance having a fullerene skeleton (fullerenes) with a sorbate ester can be produced by mixing a fullerenes and a sorbate ester with heating thereby conducting an addition reaction. A composition, containing a fullerene derivative like this, for an underlayer film used in multilayer resist film can give excellent etching resistance, can suppress pattern wiggling, and can avoid a poisoning problem in upperlayer patterning.

In addition, the present invention provides a fullerene derivative having "n" numbers of a partial structure shown by the following general formula (1a).

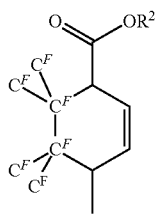

(1a)

(Wherein, $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom. $C^F$ represents a carbon atom that composes a fullerene skeleton of the fullerene derivative. Reference character "n" represents an integer of 1 to 30.)

A fullerene derivative having "n" numbers of a partial structure shown by the general formula (1a) can be produced, for example, by mixing a fullerenes and a sorbate ester with heating thereby conducting an addition reaction. Alternatively, the fullerene derivative can be produced via a reaction product between a sorbate ester derivative of different type and a fullerenes. A composition, containing a fullerene derivative like this, for an underlayer film used in a multilayer resist film can give excellent etching resistance, can suppress pattern wiggling, and can avoid a poisoning problem in upperlayer patterning.

As explained above, the composition for a resist underlayer film of the present invention can give excellent etching resistance, can suppress pattern wiggling during formation of a fine pattern having a size of approximately 40 nm or less, and can avoid a poisoning problem in upperlayer patterning by using a chemical amplification resist; and thus, the composition is extremely useful as a composition for a resist underlayer film used in a multilayer resist process, such as, for example, a silicon-containing bilayer resist process, a three-layer resist process using a silicon-containing intermediate film, and a quadrolayer resist process using a silicon-containing intermediate film and an organic anti-reflective film.

BRIEF EXPLANATION OF THE DRAWING

FIG. 1 is an explanatory diagram of a three-layer resist process.

DETAILED DESCRIPTION OF THE PREFERRED EMBODIMENTS

As mentioned above, a composition for a resist underlayer film giving further excellent etching resistance with suppressed wiggling during substrate etching while avoiding a poisoning problem in upperlayer patterning by using a chemical amplification resist has been desired.

Inventors of the present invention synthesized various fullerene derivatives which are soluble in coating solvents (organic solvents) and investigated their physical properties; and as a result, they found that a fullerene derivative described later could generate, during formation of an underlayer film by baking, a substance having high carbon density and low hydrogen density, comparable to those of a fullerene itself, by thermal decomposition and elimination of a derivatized side chain that was necessary for dissolution, so that excellent dry etching resistance and high suppressing effect of wiggling during etching could be obtained. In addition, the inventors found that the fullerene derivative as mentioned above did not adversely affect resist patterning upon expressing the foregoing effects, that is, a poisoning problem could be avoided, thereby accomplished the present invention.

Namely, the composition for a resist underlayer film of the present invention comprises at least (A) a fullerene derivative that is a reaction product of a substance having a fullerene skeleton with a 1,3-diene compound derivative having an electron-withdrawing group and (B) an organic solvent.

Here, a substance containing "n" numbers of a partial structure shown by the following general formula (1) may be mentioned as a preferred embodiment of the fullerene derivative (A) that is a reaction product of a substance having a fullerene skeleton with a 1,3-diene compound derivative having an electron-withdrawing group.

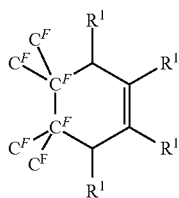

(1)

(Wherein, each $R^1$ independently represents a hydrogen atom, a nitro group, a cyano group, a carboxyl group, a hydroxy group, and a sulfo group; and a monovalent organic group having 1 to 20 carbon atoms which may contain any one or more of a cyano group, a carboxyl group, a hydroxy group, a nitro group, a sulfo group, a carbonyl group, an ether group, an ester group, a sulfone group, and a halogen atom, wherein one or more $R^1$ is an electron-withdrawing group. Two or more $R^1$ may be bonded with each other to form a ring. $C^F$ represents a carbon atom that composes a fullerene skeleton of the fullerene derivative. Reference character "n" represents an integer of 1 to 30.)

The partial structure shown by the general formula (1) is effective to secure solubility of the fullerene derivative into a solvent used for an underlayer film; and in addition, the partial structure has a role to substantially decrease hydrogen density of an underlayer film by decomposition during formation of the underlayer film and heat treatment thereof. A decomposition product of the partial structure (1) is not a basic compound such as an amine so that a harmful effect to a pattern profile during upperlayer resist patterning can be suppressed.

In addition, a reaction product of a substance having a fullerene skeleton with a sorbate ester may be mentioned as a more preferred embodiment of the fullerene derivative (A) that is a reaction product of a substance having a fullerene skeleton with a 1,3-diene compound derivative having an electron-withdrawing group.

Further, a substance containing "n" numbers of a partial structure shown by the following general formula (1a) may be mentioned as a more preferred embodiment of the fullerene derivative (A) that is a reaction product of a substance having a fullerene skeleton with a 1,3-diene compound derivative having an electron-withdrawing group.

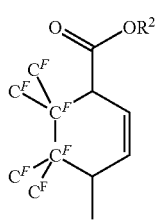

(1a)

(Wherein, $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom. $C^F$ and "n" represent the same meanings as before.)

The partial structure shown by the general formula (1a) is very effective to secure solubility of the fullerene derivative into a solvent used for an underlayer film; and in addition, the partial structure has a role to substantially decrease hydrogen density of an underlayer film by decomposition thereof during formation of the underlayer film and heat treatment thereof. A decomposition product of the partial structure (1a) is not a basic compound such as an amine so that a harmful effect to a pattern profile during upperlayer resist patterning can be suppressed.

The composition for a resist underlayer film of the present invention may be made to contain a single fullerene derivative having "n" numbers (an integer of 1 to 30) of the partial structure shown by the general formula (1), in particular (1a), or a mixture of two or more fullerene derivatives having different "n"; but in view of solubility in a resist solvent and coating properties, a mixture of two or more fullerene derivatives is advantageous. In this case, "n" of the fullerene derivative contained with the highest presence ratio is preferably 2 to 10 in particular, because, when "n" is 2 or more, there is no fear of poor coating properties and poor solubility in a resist solvent; when "n" is 10 or less, there is no fear of deterioration of the foregoing betterment of etching resistance and wiggling suppression effect.

In the general formulae (1) and (1a), $C^F$ represents a carbon atom that composes a fullerene skeleton of the fullerene derivative. The fullerene skeleton is composed of only carbon atoms and has a carbon network with a closed shell structure formed by a plurality of a 5-membered ring and a 6-membered ring, wherein all of carbon atoms are bonded to other three carbon atoms. Here, $C^F$ represents also any six carbons nearby present in the fullerene skeleton.

The number of fullerene carbons is usually 60 or more and 120 or less; there is no restriction as to the fullerene skeleton of a substance having a fullerene skeleton (fullerene skeleton of a fullerene derivative), which is a raw material of the fullerene derivative of the present invention; and illustrative example of the skeleton includes $C_{60}$, $C_{70}$, $C_{76}$, $C_{82}$, $C_{84}$, and $C_{90}$. Among them, $C_{60}$ and $C_{70}$ are preferable, though $C_{60}$ is more preferable, because these can be easily obtained as main products in fullerene production.

Meanwhile, the fullerene skeleton may be one kind or in an arbitrary combination of two or more kinds with an arbitrary mixing ratio; or a fullerene mixture obtained in fullerene production may be used without a problem.

Below, a fullerene skeleton of the fullerene $C_{60}$ is shown. In the below formula, a single bond and a double bond are not distinguished, and both are shown by continuous lines or dashed lines.

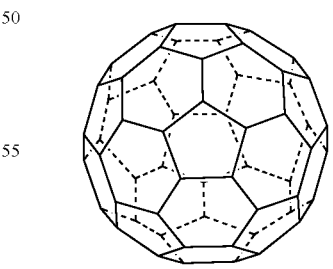

Fullerene $C_{60}$ skeleton

A compound shown by the following general formula (4), or preferably a sorbate ester shown by the following general formula (5), may be mentioned as specific examples of the 1,3-diene compound derivative having an electron-withdrawing group.

(Wherein, $R^1$ and $R^2$ represent the same meanings as before.)

The 1,3-diene compound derivative shown by the general formula (4) or preferably by the general formula (5) can easily undergo an addition reaction with a fullerenes (substance having a fullerene skeleton); namely a double bond in the fullerene skeleton reacts with a conjugated diene (1,3-diene compound derivative) to give a product mainly comprised of a substance having "n" numbers of the Partial structure shown by the general formula (1) or preferably by the general formula (1a). The product is highly soluble in a solvent used for an underlayer film and has sufficient stability near normal temperature. In addition, the product is decomposed thermally during formation of an underlayer film and heat treatment thereof thereby eliminating the 1,3-diene compound derivative shown by the general formula (4) or (5), so that the product plays a role to substantially decrease hydrogen density of the underlayer film. In addition, the 1,3-diene compound derivative, shown by the general formula (4) or (5), obtained by the decomposition is, because of its structure, not a basic compound such as an amine; and thus a harmful effect to a pattern profile during upperlayer resist patterning can be suppressed.

In the general formulae (1) and (4), each $R^1$ independently represents a hydrogen atom, a nitro group, a cyano group, a carboxyl group, a hydroxy group, and a sulfo group; and a monovalent organic group having 1 to 20 carbon atoms which may contain any one or more of a cyano group, a carboxyl group, a hydroxy group, a nitro group, a sulfo group, a carbonyl group, an ether group, an ester group, a sulfone group, and a halogen atom, wherein one or more $R^1$ is an electron-withdrawing group. Two or more $R^1$ may be bonded with each other to form a ring.

More specific example of $R^1$ includes a hydrogen atom, a nitro group, a hydroxy group, a sulfo group, a cyano group, and a carboxyl group; and a monovalent organic group having 1 to 20 carbon atoms selected from a methyl group, an ethyl group, a vinyl group, a 2,2,2-trifluoroethyl group, a propyl group, an isopropyl group, an allyl group, a 1-propenyl group, an isopropenyl group, a butyl group, a s-butyl group, a t-butyl group, an isobutyl group, a pentyl group, a cyclopentyl group, a hexyl group, a cyclohexyl group, a decyl group, a dodecyl group, an icosanyl group, a norbornyl group, an adamantly group, a phenyl group, a toluoyl group, a xylyl group, a naphthyl group, a phenanthrenyl group, an anthracenyl group, a benzyl group, a fluorenyl group, and a naphthyl methyl group; further included are the foregoing groups whose part of hydrogen atoms is substituted with a cyano group (—CN), a carboxyl group (—COOH), a hydroxy group (—OH), a nitro group (—$NO_2$), a sulfo group (—$SO_3H$), and a halogen atom; and included also are the foregoing groups whose part of a methylene group is substituted with a carbonyl group (—CO—), an oxygen atom (—O—), an ester group (—COO—), and a sulfone group (—$SO_2$—).

When $R^1$ is an electron-withdrawing group, specific example of the electron-withdrawing group includes a cyano group, a carboxyl group, a nitro group, a sulfo group, an acyl group, an alkoxy carbonyl group, an alkane sulfonyl group, and a trifluoromethyl group. When two or more $R^1$ connect with each other to form a ring, specific example of the ring thereby formed includes a cyclopropane ring, a cyclopropane ring, a cyclobutene ring, a cyclobutene ring, a cyclopentane ring, a cyclopentene ring, a cyclopentadiene ring, a hexane ring, a hexene ring, a hexadiene ring, a norbornane ring, a norbornane ring, and a bicyclo[2.2.2]octene ring.

A reaction product of a usual 1,3-diene compound with fullerenes has poor stability near room temperature in some cases; but the stability can be secured when one or more $R^1$ is an electron-withdrawing group. On the other hand, thermal decomposition can take place easily during formation of an underlayer film and heat treatment thereof thereby giving a fullerene having high carbon density and low hydrogen density, so that excellent etching resistance and wiggling prevention effect can be obtained. In addition, solubility into a coating solvent and coating properties can be improved as compared with the case that all of $R^1$ are a hydrogen atom or a hydrocarbon group. Performance such as solubility into a solvent and temperature of thermal decomposition can be controlled by selection of each $R^1$ structure.

$R^2$ in the general formulae (1a) and (5) represents a linear, a branched, or a cyclic alkyl group having 1 to 19 carbon atoms, an aryl group having 6 to 15 carbon atoms, a hetero aryl group having 4 to 15 carbon atoms, or an aralkyl group having 7 to 19 carbon atoms, wherein these groups may contain a carbonyl group, an ether group, an ester group, a cyano group, a carboxyl group, a hydroxy group, or a halogen atom. More specific example of $R^2$ includes a methyl group, an ethyl group, a propyl group, an allyl group, a homoallyl group, an isopropyl group, a butyl group, a sec-butyl group, a tert-butyl group, a tert-amyl group, a pentyl group, a hexyl group, a cyclopentyl group, a cyclohexyl group, a norbornyl group, an adamantly group, a vinyl group, an isopropenyl group, a propenyl group, a methallyl group, an ethynyl group, an acetyl group, a propionyl group, a methoxymethyl group, a methoxy carbonyl methyl group, a cyanomethyl group, a carboxy methyl group, a 2-hydroxy ethyl group, a 2-methoxy ethyl group, a 2-ethoxy ethyl group, a 2-butoxy ethyl group, a 2-(2-methoxyethoxy)ethyl group, a 2-(2-ethoxyethoxy)ethyl group, a 2-(2-butoxyethoxy)ethyl group, a 2-[2-(2-methoxyethoxy)ethoxy]ethyl group, a 2-[2-(2-ethoxyethoxy)ethoxy]ethyl group, a 2-[2-[2-(2-methoxyethoxy)ethoxy]ethoxy]ethyl group, a phenyl group, a tolyl group, a xylyl group, a naphthyl group, an indanyl group, an indenyl group, an anthranyl group, a phenanthryl group, a pyrenyl group, a naphthacenyl group, an acetoxy phenyl group, a methoxy phenyl group, a methoxy carbonyl phenyl group, a cyanophenyl group, a carboxy phenyl group, a hydroxy phenyl group, a hydroxy naphthyl group, a methoxy naphthyl group, a furanyl group, a thiophenyl group, a benzofuranyl group, a benzothiophenyl group, a phenoxathinly group, a benzyl group, a 2-phenyl ethyl group, a 3-phenyl propyl group, a naphthyl methyl group, a pyrenyl methyl group, a 2-phenyl vinyl group, a 1-phenyl vinyl group, a phenyl ethynyl group, a methoxy carbonyl group, an ethoxy carbonyl group, a propoxy carbonyl group, a butoxy carbonyl group, an isopropoxy carbonyl group, a cyclohexyl oxycarbonyl group, and an adamantly oxycarbonyl group.

The fullerene derivative (A) used in the composition for a resist underlayer film of the present invention is a reaction product of a substance having a fullerene skeleton with a 1,3-diene compound derivative having an electron-withdrawing group, namely, a reaction product of a substance having a fullerene skeleton on which a functional group is attached, as the substance having a fullerene skeleton, with a 1,3-diene compound derivative having an electron-withdrawing group may be used; and in this case, the fullerene derivative (A) may contain, in addition to the partial structure shown by the general formula (1), in particularly by (1a), other functional groups such as an epoxide group, a hydroxy group, and an amino group on the fullerene skeleton to a degree not adversely affecting the foregoing effects.

Here, example of the fullerene derivative having the partial structure shown by the general formula (1) is shown below ($C_{60}$ fullerene skeleton, n=1).

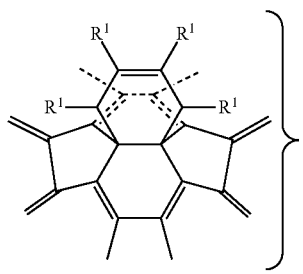

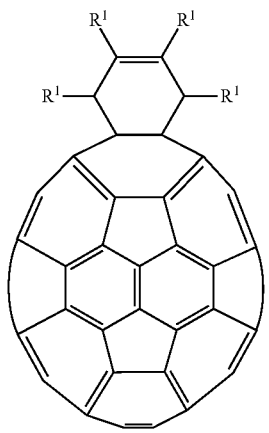

Compounds shown below can be mentioned as further specific examples of the fullerene derivative having the partial structure shown by the general formulae (1) and (1a); but the fullerene derivative is not limited to them. Wherein, reference character "n" represents the same meaning as before. Wherein, the FIGURE shown below

represents a fullerene skeleton, Me represents a methyl group, Et represents an ethyl group, Bu represents a butyl group, Ph represents a phenyl group, and Ac represents an acetyl group. The same is applied hereinafter.

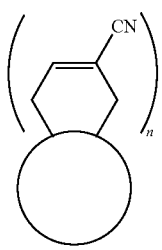
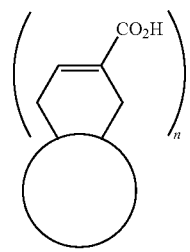

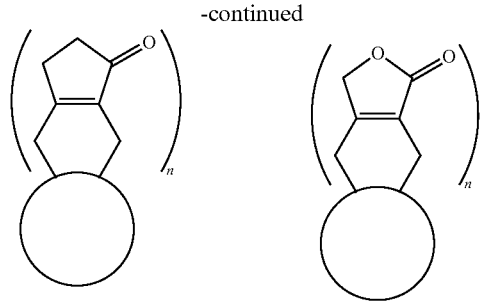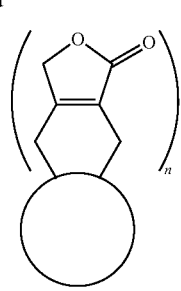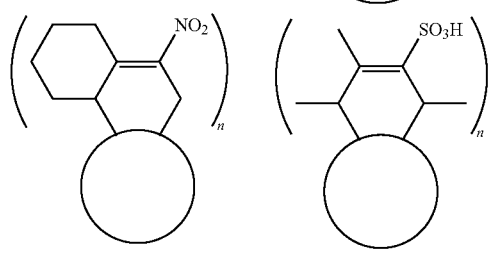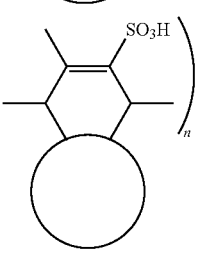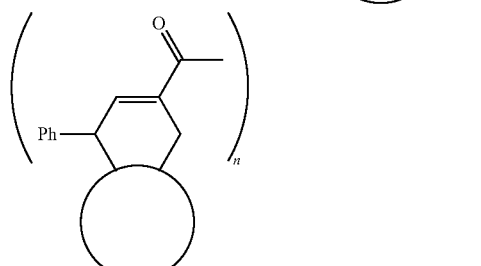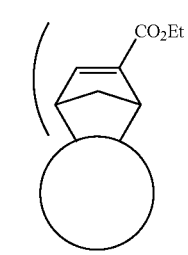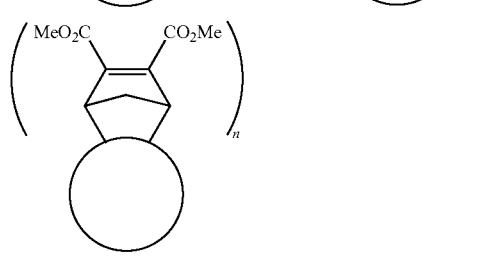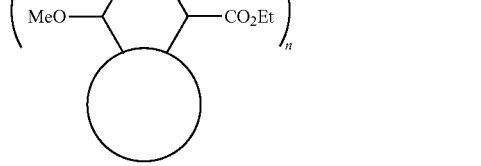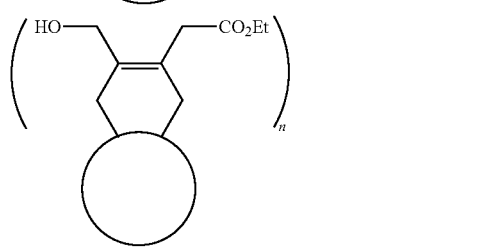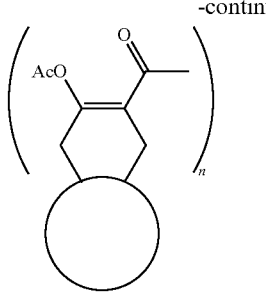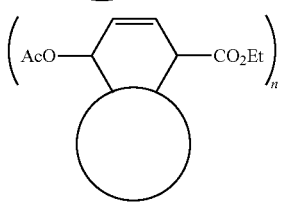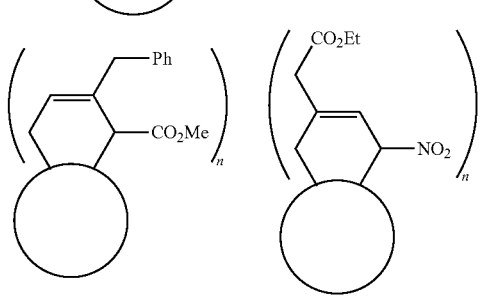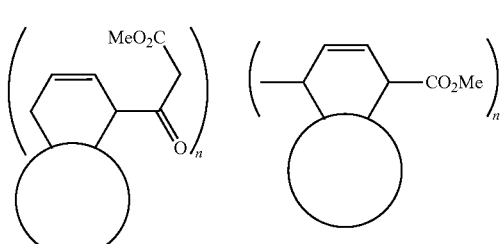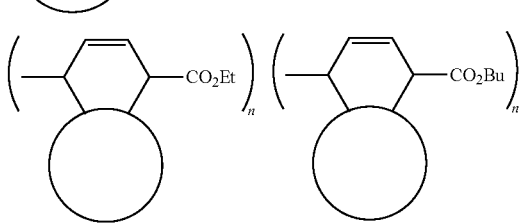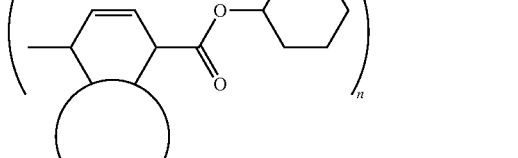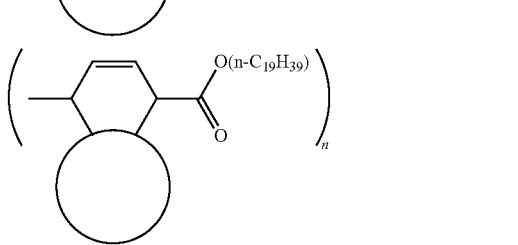

-continued
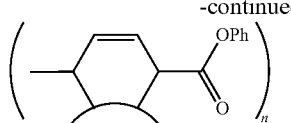
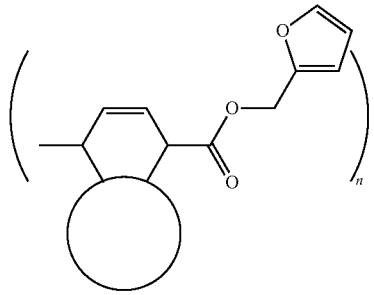
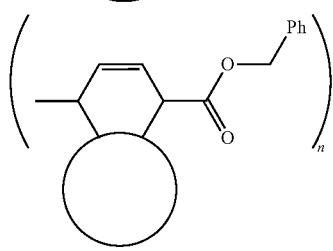
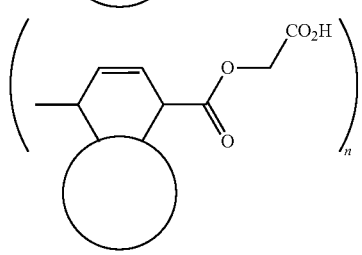
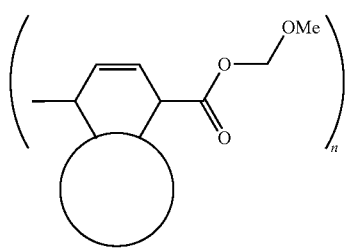
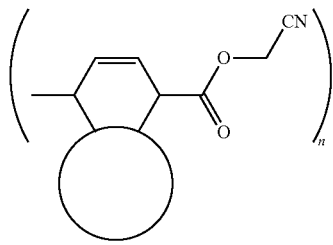
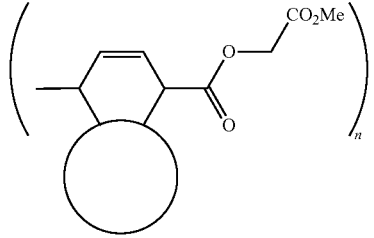
-continued
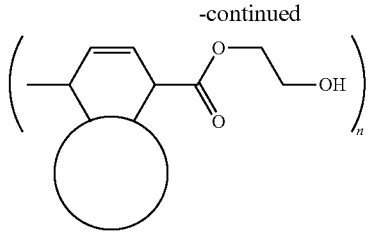
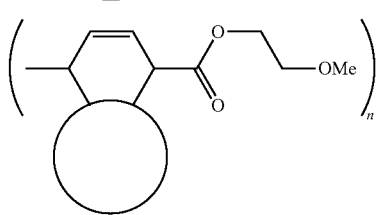
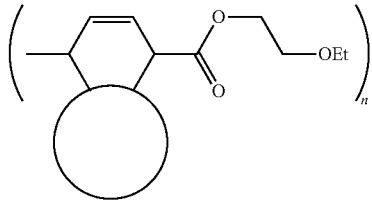
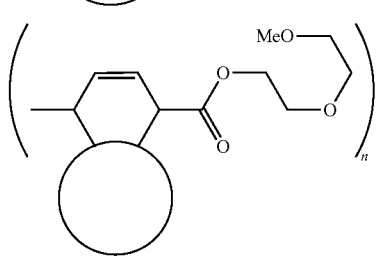
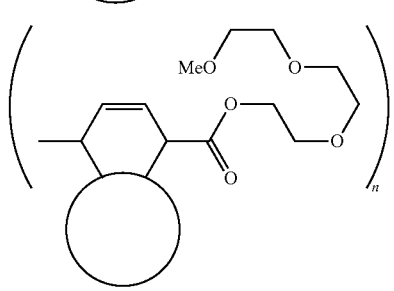
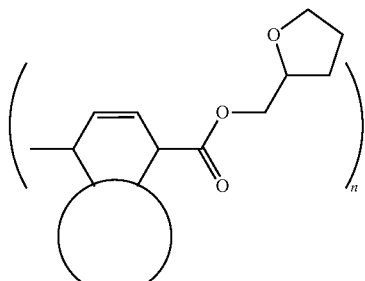
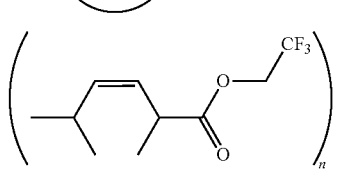

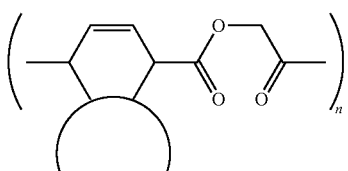

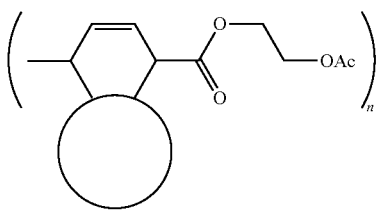

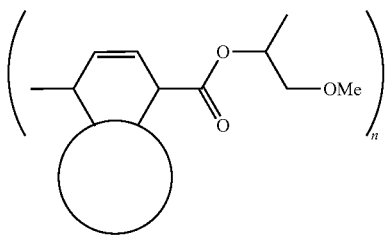

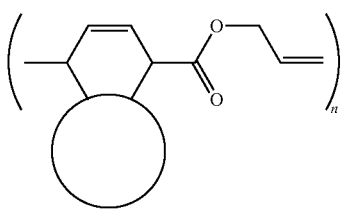

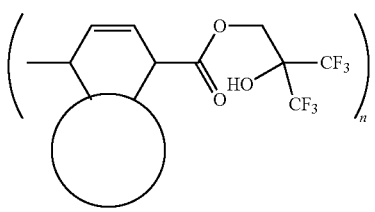

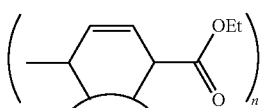

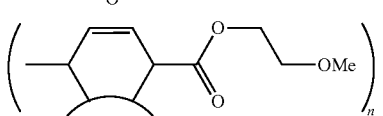

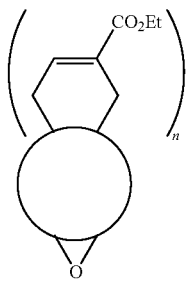

Blending amount of a fullerene derivative such as the one having a partial structure shown by the general formulae (1) or (1a), which is a reaction product of fullerenes (substance having a fullerene skeleton) with a 1,3-diene compound derivative having an electron-withdrawing group, into a composition for a resist underlayer film is preferably 10 parts by mass or more and 100 parts by mass or less or more preferably 15 parts by mass or more and 85 parts by mass or less, relative to 100 parts by mass of total solid components other than an organic solvent among entire components of the composition for a resist underlayer film. Effects of improvement in etching resistance and suppression of wiggling are eminent when the amount is 10 parts by mass or more; the effects are more eminent when the amount is 15 parts by mass or more, and thus, this amount is more preferable. When the amount is 85 parts by mass or less, uniformity of a coated film is improved; and thus this amount is preferable.

The addition reaction of the fullerenes to the 1,3-diene compound derivative having an electron-withdrawing group, such as a sorbate ester, can be carried out by selecting the best method in accordance with their structures to produce the fullerene derivative mainly comprised of the substance having "n" numbers of a partial structure shown by the general formula (1) or (1a). Specifically, the fullerene derivative can be produced by using a fullerene shown by (6) and a 1,3-diene compound derivative having an electron-withdrawing group shown by (4) or (5), according to, for example, a method described in Tetrahedron, Vol. 52, No. 14, 4983 (1996), as shown below.

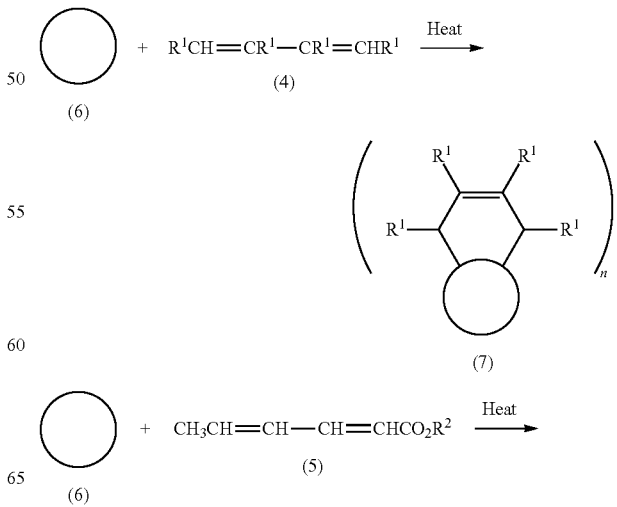

-continued

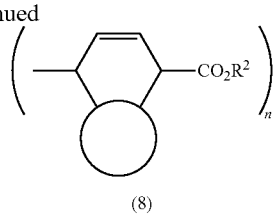

(8)

Wherein, reference character "n", $R^1$, $R^2$ and the FIGURE shown below represent the same meanings as before.

As to the fullerene (6) used in the above reaction, $C_{60}$ or $C_{70}$ may be used singly, or as a mixture of $C_{60}$ and $C_{70}$, or the fullerene mixture of $C_{60}$, $C_{70}$ and a higher fullerene, as mentioned above. As to the 1,3-diene compound derivative having an electron-withdrawing group (4), a commercially available compound may be used; or the derivative may be produced according to a heretofore known method described later (for example, a method described in Tetrahedron, Vol. 52, No. 14, 4983 (1996)). A commercially available sorbate ester (5) may be used or the sorbate ester may be synthesized by an ordinary method described later.

The optimum amount of the 1,3-diene compound derivative having an electron-withdrawing group (4) and of the sorbate ester (5) in the reaction is preferably 0.5 to 100 mole, or in particular 1 to 100 mole, relative to one mole of the fullerene (6).

The above addition reaction can be conducted by mixing each material in a solvent or under non-solvent, and heated them. In the case of using solvent in the reaction, one kind solvent or mixture of two or more kind solvent may be used by selecting from aliphatic hydrocarbons such as hexane and heptane; aromatic hydrocarbons such as toluene, xylene, trimethylbenzene, methylnaphthalene; ethers such as dibutylether, diethylene glycol diethyl ether, diethylene glycol dimethyl ether, tetrahydrofuran; ketons such as acetone and 2-butanone; alcohols such as methanol, ethanol, 2-propanol, t-butylalcohol, methoxyethanol, diethylene glycol monomethyl ether; esters such as ethyl acetate; nitriles such as acetonitrile; amides such as N,N-dimethylformamide and N,N-dimethylacetamide; halogenated hydrocarbons such as o-dichlorobenzene, dichloromethane and 1,2-dichloroethane; amines such as pyridine and quinoline; and water. Solvent of aromatic hydrocarbons and mixed solvent containing aromatic hydrocarbons are more preferable in view of securing solubility of raw material fullerene (6).

Reaction temperature is preferably 50 to 200° C., or more preferably 80 to 150° C. When a solvent is used, the upper limit temperature is preferably near boiling point of the solvent. When the reaction temperature is 50° C. or higher, there is no fear that the reaction becomes very slow; when the reaction temperature is 200° C. or lower, there is no fear that decomposition of the product becomes eminent; and thus, this temperature range is preferable. Reaction time of the addition reaction is preferably determined by following progress of the reaction with a thin-layer chromatography, a liquid chromatography, a gel-permeation chromatography, and the like to increase a reaction yield; the time is usually about 2 to about 200 hours. After the reaction, the intended fullerene derivative (7) or (8) mainly comprised of a substance having "n" numbers of a partial structure shown by the general formula (1) or (1a) is obtained by usual aqueous work-up and/or filtration treatment of insoluble matters. The fullerene derivative (7) or (8) may be purified, as appropriate, by a conventional method such as phase separation, crystallization, and chromatography.

Fullerene (6) is unstable with oxygen and light in some cases; and thus, the reaction is preferably carried out under inert atmosphere and light shielding. To suppress a side reaction, a generally used stabilizer and anti-oxidant, such as 2,6-di-tert-butyl-4-methylphenol and 4-methoxy phenol, may be added to the reaction system. Added amount of such an agent, if used, is preferably about 1 to about 10000 ppm relative to fullerene (6).

Other than the foregoing methods, a fullerene derivative (8) may be produced, via an intermediate (9) having different $R^2$ structure obtained by a method similar to those mentioned before, with an ordinary method reported in a literature (Protective Groups in Organic Synthesis, 3rd Ed., Wiley-Interscience, New York, 1999, 372-381), which involves a deprotection reaction (intermediate (10)) and a reprotection reaction as shown in the following reaction scheme; but this method has more process steps thereby expecting increase in production cost, and thus, it may be assumed that this method is disadvantageous industrially.

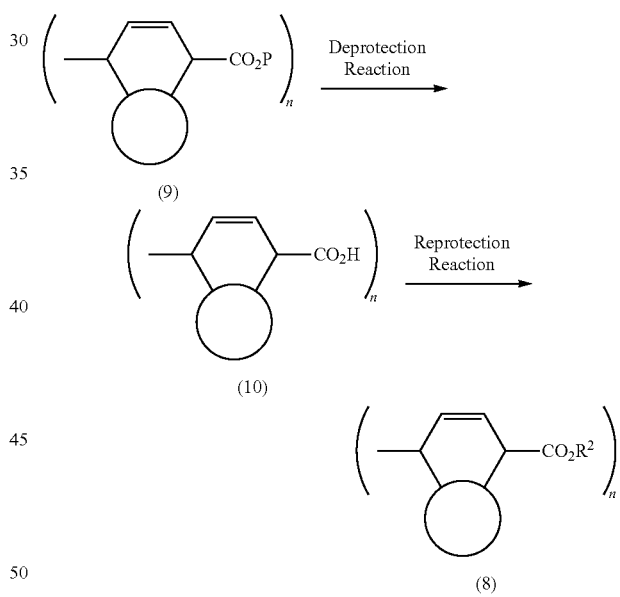

Wherein, P represents a protecting group, while reference character "n", $R^2$, and FIGURE shown below represent the same meanings as before.

In the foregoing literature, which is in the public domain (Tetrahedron, Vol. 52, No. 14, 4983 (1996)), with regard to production of the fullerene derivative (7), following compounds are used as the raw material 1,3-diene compound derivatives having an electron-withdrawing group (4).

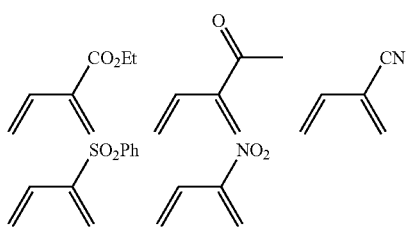

However, as described in the foregoing literature, any of these compounds has low stability and undergoes dimerization easily; and thus isolation and purification thereof are impossible. In addition, naturally the dimerization reaction takes place competitively during the reaction with a fullerene (6), thereby causing a problem of low selectivity of the intended reaction; and thus these compounds are industrially rather unsuitable.

On the other hand, in the present invention, in the fullerene derivative which is a reaction product of a substance having a fullerene skeleton (fullerenes) and a sorbate ester, and in the fullerene derivative (8) having "n" numbers of a partial structure shown by the general formula (1a), the sorbate ester (5) is used as the raw material 1,3-diene compound derivative having an electron-withdrawing group (4). A sorbate ester is generally stable so that isolation and purification thereof can be done without a problem. In addition, various derivatives can be produced easily and cheaply by a one-step simple esterification or ester-exchange reaction by using a raw material such as sorbic acid, potassium sorbate, and ethyl sorbate, which are industrially available easily and in large quantity; and thus a sorbate ester has a large merit industrially. In addition, reactivity with fullerenes is adequate, and solubility into a solvent and storage stability of a reaction product thereof are excellent. Still in addition, by decomposition during formation of an underlayer film and heat treatment thereof, substantially carbon density of the underlayer film can be increased and hydrogen density thereof can be decreased as well; and yet, a basic substance giving a harmful effect during upperlayer resist patterning is not generated. Accordingly, the fullerene derivative which is a reaction product of fullerenes and a sorbate ester, and the fullerene derivative having "n" numbers of a partial structure shown by the general formula (1a), in the present invention, are extremely suitable substances when a fullerene derivative is industrially applied to a composition for an underlayer film.

The organic solvent (B) usable in the composition for a resist underlayer film of the present invention is not particularly restricted so far as a fullerene derivative of the component (A) is soluble therein; accordingly, a solvent that can dissolve a resin having an aromatic ring, a phenolic-hydroxy group containing compound, an acid generator, a crosslinking agent, a surfactant, as described later and the like may be used. Specifically, those solvents described in paragraphs (0091) to (0092) of Japanese Patent Laid-Open Publication No. 2007-199653 may be used. Among them, propylene glycol monomethyl ether acetate, propylene glycol monomethyl ether, 2-heptanone, cyclopentanone, cyclohexanone, γ-butyrolactone, and a mixture of two or more of these solvents may be preferably used.

It is preferable that the composition for a resist underlayer film of the present invention contain (C) a resin having an aromatic ring to improve coating properties at the time of spin coating, filling-up characteristic of a stepped substrate, and etching resistance. It is more preferable that (C) the resin having an aromatic ring contain a naphthalene ring in view of etching resistance and optical properties.

More specific example of (C) the resin having an aromatic ring that is blended suitably into the composition for a resist underlayer film of the present invention includes, in addition to (C1) as described later, a resin obtained by polycondensation of one or more of a compound having an aromatic ring as shown below with a formaldehyde-equivalent compound (namely, formaldehyde, paraformaldehyde, 1,3,5-trioxane, formaldehyde dimethyl acetal, and the like) under an acidic condition.

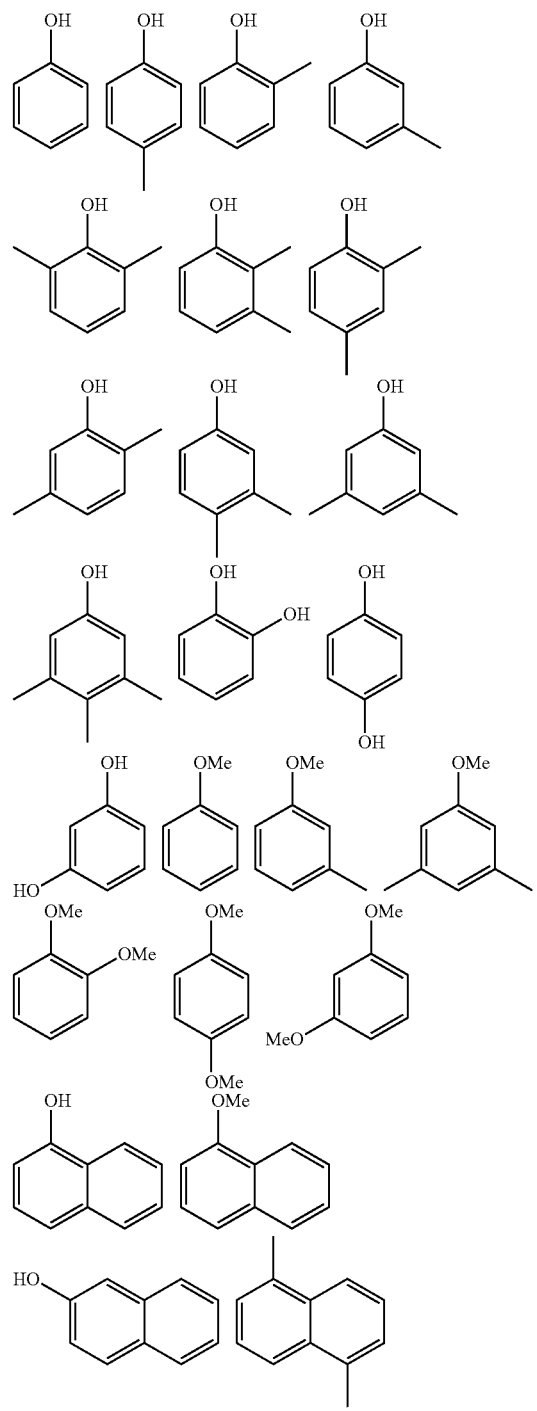

-continued

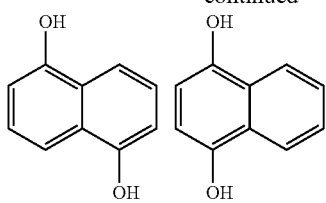

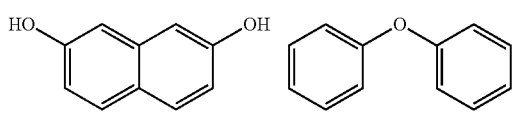

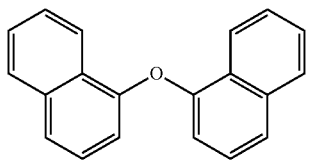

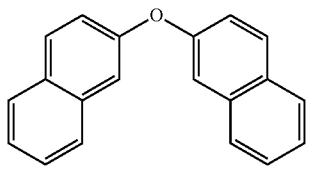

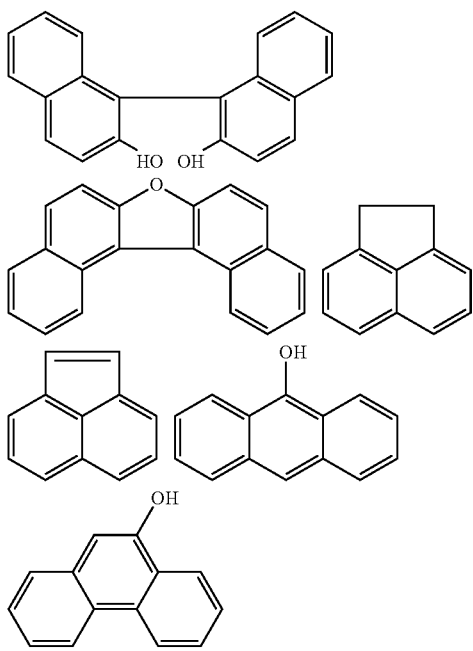

It is preferable that (C) the resin having an aromatic ring that is blended into the composition for a resist underlayer film of the present invention contain at least a compound (C1) obtained by polycondensation of a compound shown by the following general formula (2) and a compound shown by the following general formula (3) under an acidic condition.

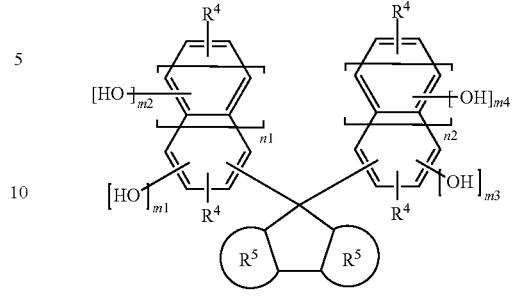

(Wherein, each $R^4$ independently represents a hydrogen atom or a hydrocarbon group having 6 to 20 carbon atoms; each $R^5$ independently represents a benzene ring or a naphthalene ring; $1 \leq m1+m2 \leq 2$ and $1 \leq m3+m4 \leq 2$; and n1 and n2 are 0 or 1, respectively.)

$$A\text{-}CHO \quad (3)$$

(Wherein, A represents any of a hydrogen atom, a linear, a branched, or a cyclic saturated or unsaturated hydrocarbon group having 1 to 20 carbon atoms, and an aromatic hydrocarbon group having 6 to 20 carbon atoms, wherein A may contain an ether group, a nitro group, a hydroxy group, or a chlorine group.)

Specific example of the compound shown by the general formula (2) includes the following compounds.

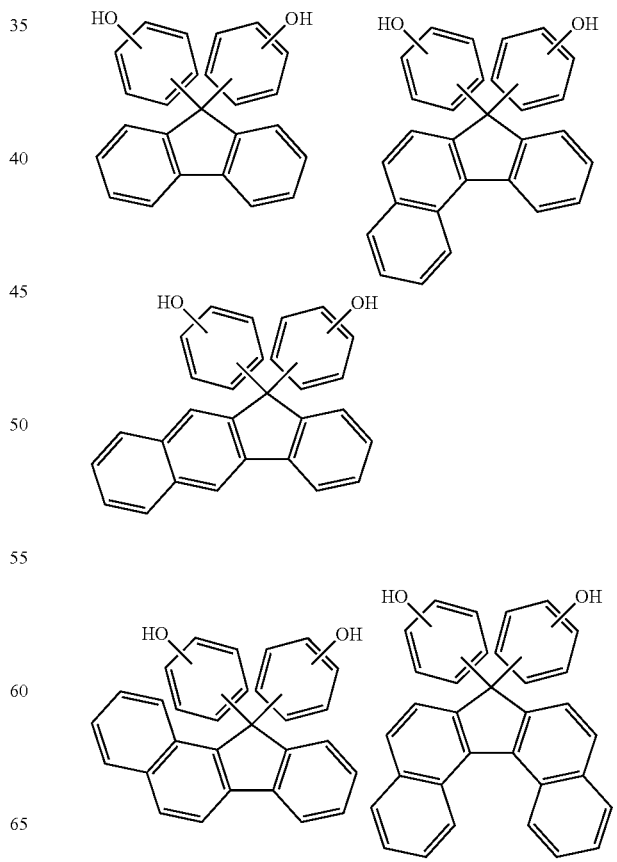

-continued
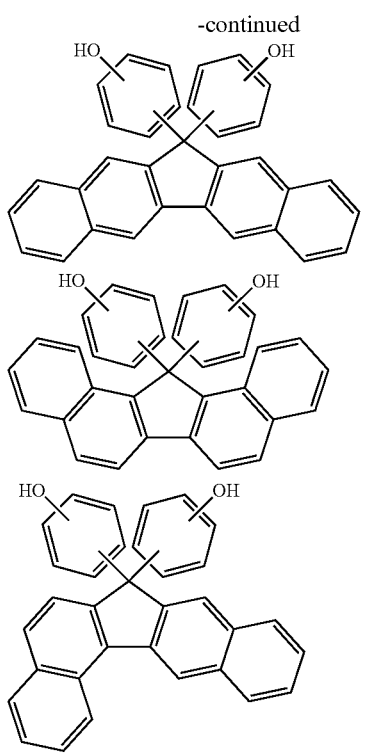
-continued
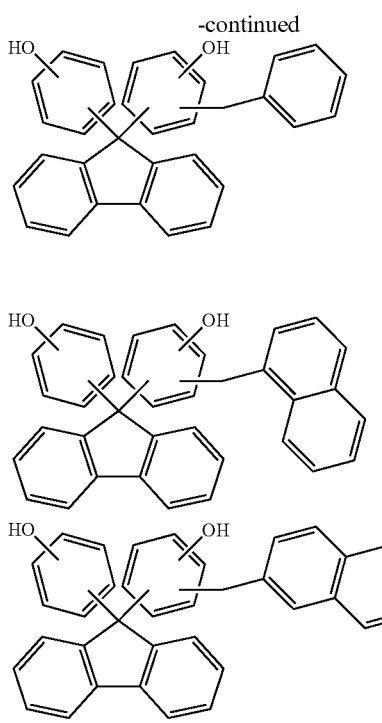
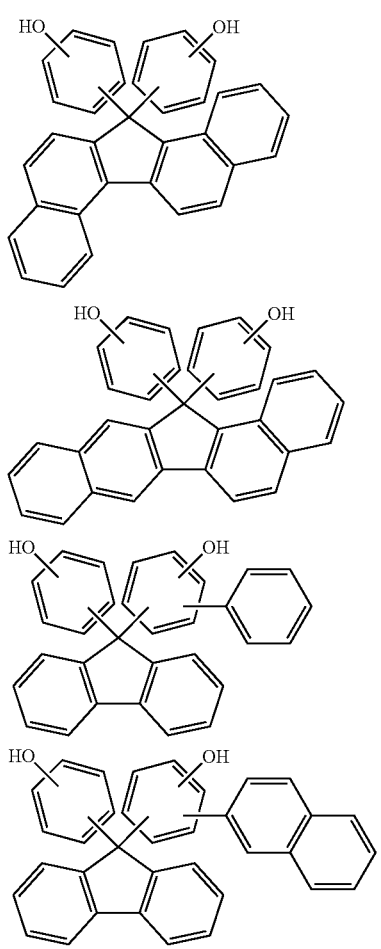
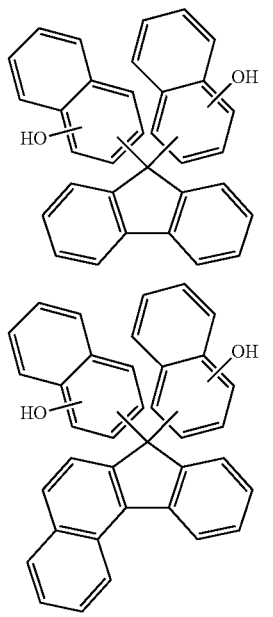
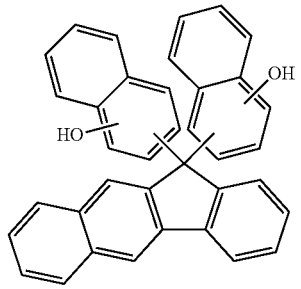

31
-continued
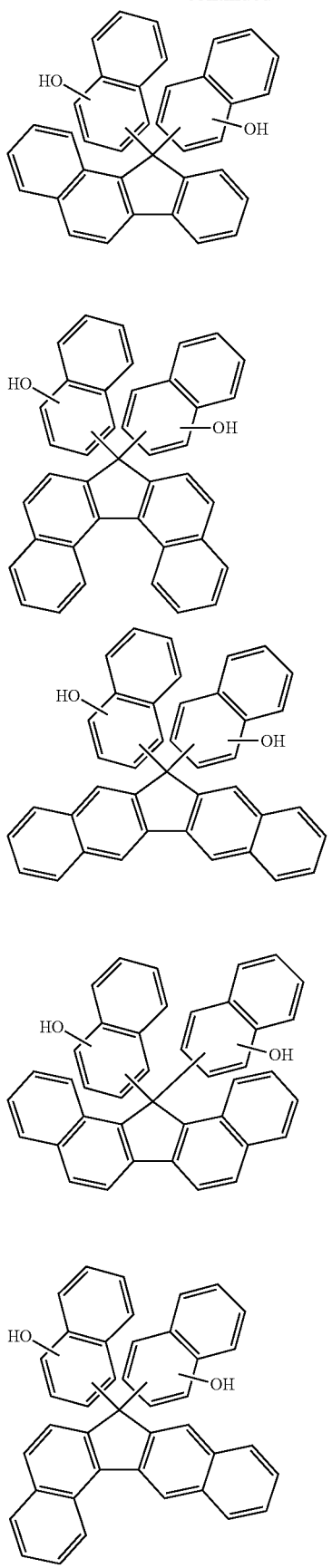
32
-continued
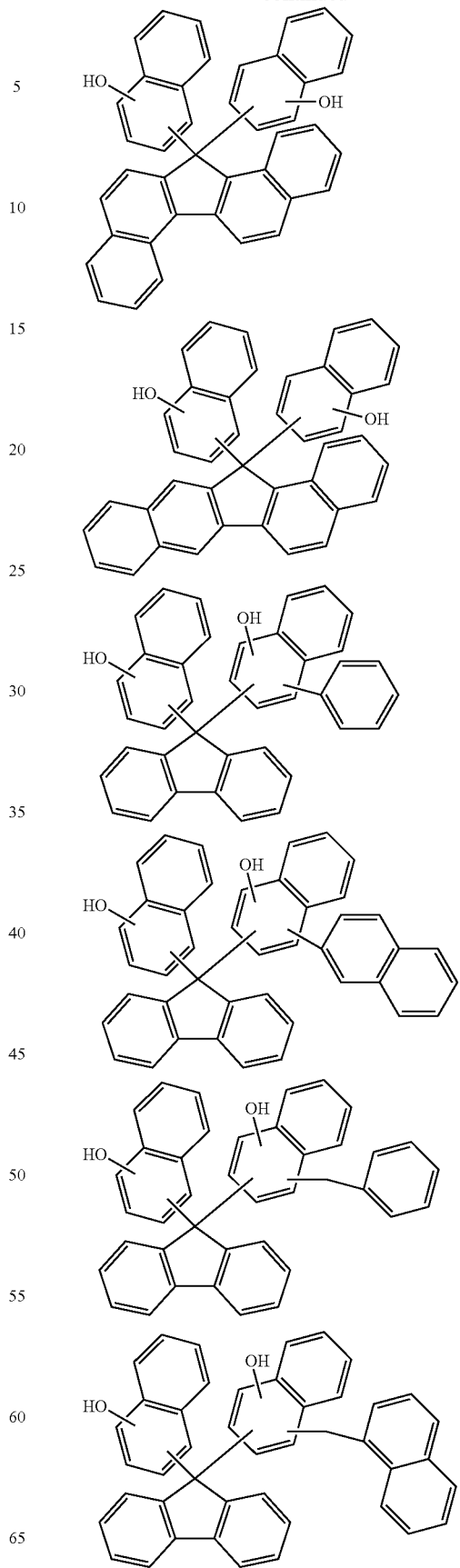

33
-continued
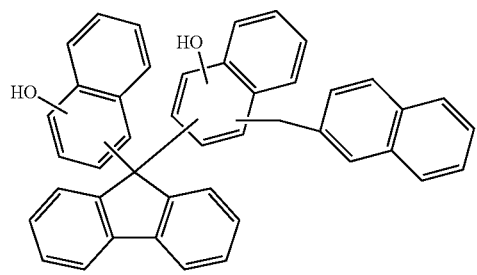
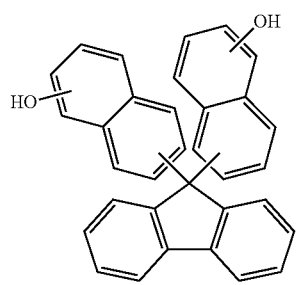
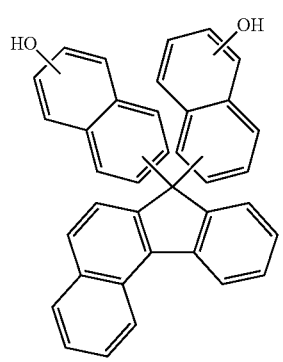
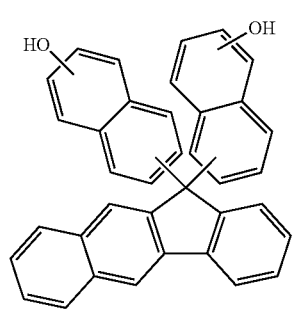
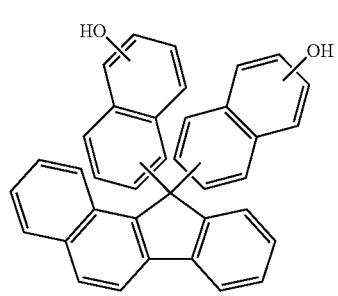
34
-continued
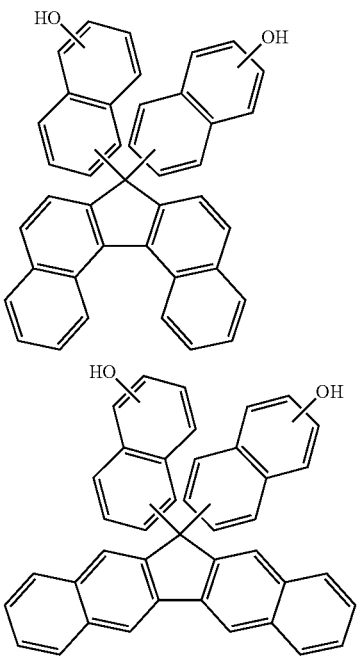
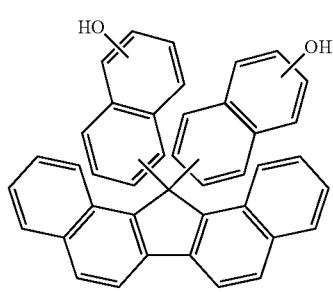
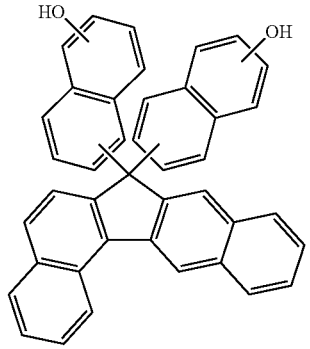
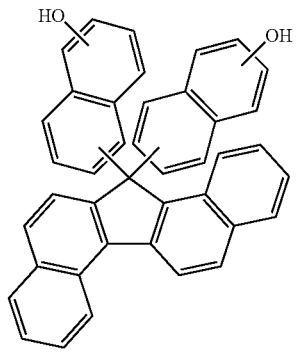

-continued
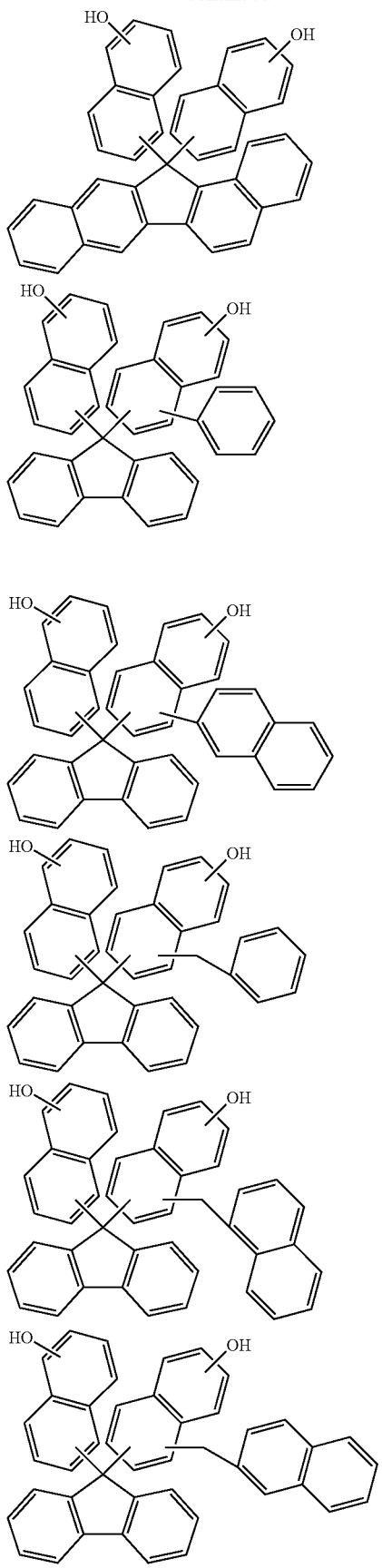
-continued
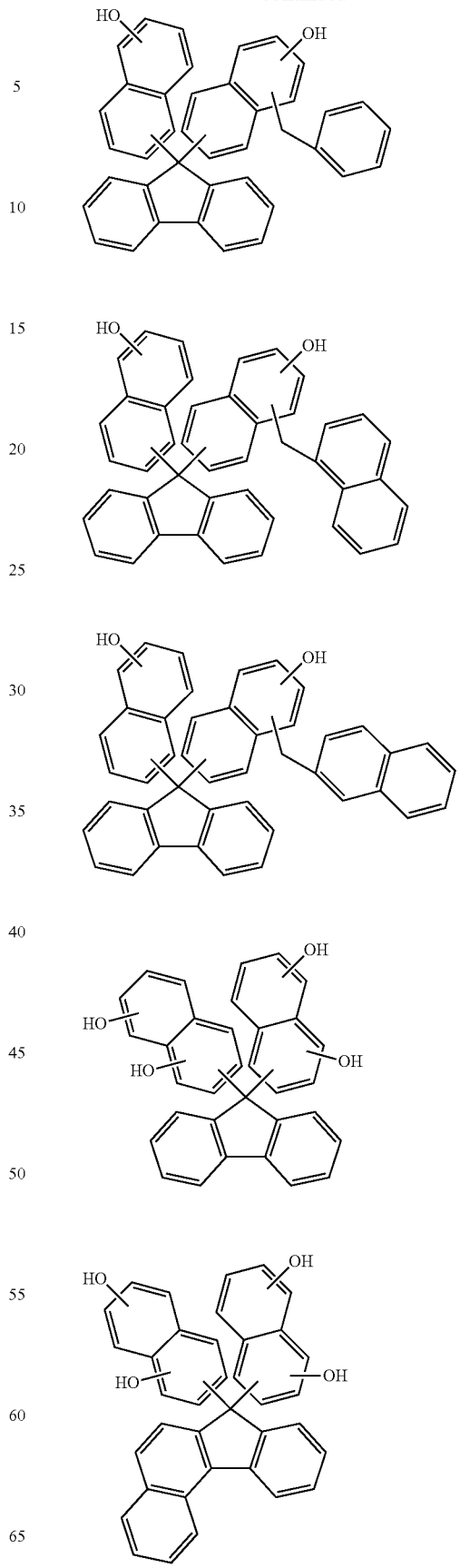

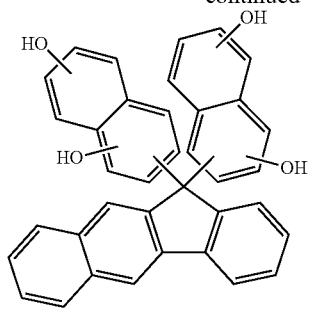

-continued

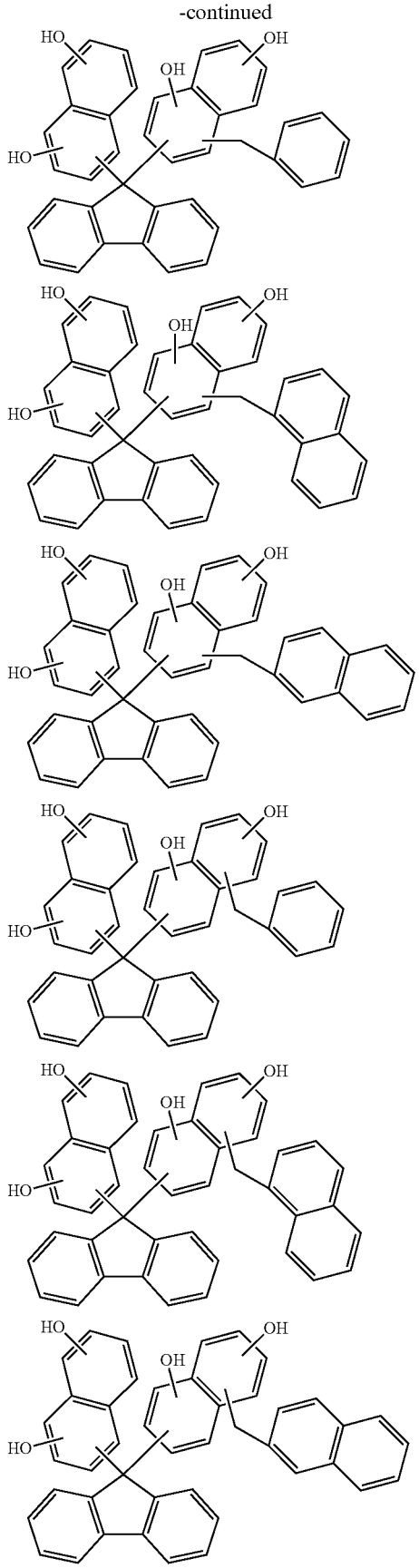

Such a compound mentioned above has a cardo structure based on a quaternary carbon and thus possesses an extremely high heat resistance.

In the case of forming an inorganic hard mask intermediate film such as a silicon oxide film, silicon nitride film or silicon oxynitride film on a resist underlayer film by CVD or the like, high temperatures exceeding 300° C. are required particularly in the case of intermediate films based on nitride films, so that the resist underlayer film is also required to possess a higher heat resistance.

Further, examples of aldehydes represented by the foregoing general formula (3) include formaldehyde, benzaldehyde, acetaldehyde, propylaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, 1-naphthaldehyde, 2-naphthaldehyde, furfural and the like. Among them, preferable are formaldehyde, benzaldehyde, 1-naphthaldehyde, 2-naphthaldehyde and the like.

Among them, in particular, formaldehyde can be used suitably. In addition, each of these aldehydes can be used solely and two or more kinds thereof can also be used in combination. An amount of the aldehydes to be used is preferably 0.2 to 5 moles or more preferably 0.5 to 2.0 moles relative to 1 mole of the compound represented by the foregoing general formula (2).

Formaldehyde can be supplied by using formaldehyde solution to be used generally. In addition, formaldehyde can also be supplied by using an arbitrary compound such as paraformaldehyde, hexamethylenetetramine and acetals such as formaldehyde dimethyl acetal as long as it exhibits the same reactivity as formaldehyde in the polycondensation reaction.

Further, the compound (C1) is obtained by condensation between a compound represented by the general formula (2) and a compound represented by the general formula (3) by an acid catalyst. Here, specific examples of the acid catalyst include an acid catalyst such as hydrochloric acid, nitric acid, sulfuric acid, formic acid, oxalic acid, acetic acid, methanesulfonic acid, camphorsulfonic acid, tosic acid and trifluoromethanesulfonic acid. An amount of these acid catalysts to be used is preferably $1\times10^{-5}$ to $5\times10^{-1}$ mole relative to 1 mole of the compound represented by the general formula (2).

As a solvent for the polycondensation reaction, for example, water, methanol, ethanol, propanol, butanol, tetrahydrofuran, dioxane, toluene, dichloromethane, dichloroethane, methylcellosolve, methoxypropyl acetate, gamma-butyrolactone, butylcellosolve or a mixture thereof can be used. These solvents are preferably in the range of 0 to 2,000 parts by mass relative to 100 parts by mass of reaction starting materials.

A reaction temperature can be appropriately determined according to reactivity of the reaction starting materials, and is usually in the range of 10° C. to 200° C.

Examples of a process of polycondensation include: a method configured to collectively charge the compound represented by the general formula (2), the compound represented by the general formula (3), and the acid catalyst, into a system; and a method configured to supply, in a dropwise manner, the compound represented by the general formula (2) and the compound represented by the general formula (3) into a system in the presence of the catalyst. After termination of the polycondensation reaction, the temperature of a reaction pot is elevated to 130 to 230° C. so as to remove unreacted fractions of the reaction starting materials, the acid catalyst, and the like which are present in the system, thereby enabling to remove volatile fractions at about 1 to 50 mmHg.

A single kind of the compound represented by the foregoing general formula (2) may be polymerized solely, and two or more kinds of the compound represented by the foregoing general formula (2) may also be used in combination for the polymerization.

A weight average molecular weight (Mw) of the compound (C1) in terms of polystyrene, which is obtained by condensation between the compound represented by the general formula (2) and the compound represented by the general formula (3) by an acid catalyst, is preferably 1,000 to 30,000 or particularly 1,500 to 20,000. A molecular weight distribution to be used is preferably in the range of 1.2 to 7.

The resist underlayer film composition of the present invention preferably includes (C) a resin containing an aromatic ring which contains such a compound (C1), thereby enabling the thus formed resist underlayer film to be excellent in filling up a stepped substrate, to have a solvent resistance and further to suppress generation of wiggling more effectively in etching a substrate, to make pattern roughness after etching favorable.

In addition, resins described in paragraphs (0028) to (0029) of Japanese Patent Laid-Open (kokai) No. 2006-227391 may be used as other resins (C) containing an aromatic ring.

Further, it is preferable that the resist underlayer film composition of the present invention includes (D) a compound containing a phenolic hydroxyl group. The compound represented by the foregoing general formula (2) is preferable as such a compound (D) containing a phenolic hydroxyl group. In addition, compounds such as phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3 naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol, 1-naphthol, 2-naphthol, 1-anthracenol, 1-pyrenol and 9-phenanthrenol can be used.

Into the resist underlayer film composition of the present invention, an acid generator (E) can be added to further promote a thermal cross-linking reaction. There are acid generators such as one generating an acid by thermal decomposition and one generating an acid by light irradiation, and any one can be added. Specifically, materials described in paragraphs (0061) to (0085) of Japanese Patent Laid-Open (kokai) No. 2007-199653 can be added.

As a crosslinker (F) usable for the resist underlayer film composition of the present invention, materials described in paragraphs (0055) to (0060) of Japanese Patent Laid-Open (kokai) No. 2007-199653 can be added. These materials can be added into the composition for a resist underlayer film in order to further accerate a cross-linking reaction by heat. In this case, crosslinkable substituent is introduced to a polymer in the composition for a resist underlayer film in some cases.

Further, into the resist underlayer film composition of the present invention, a surfactant (G) can also be added to improve coatability in spin coating. Here, surfactants described in paragraphs (0142) to (0147) of Japanese Patent Laid-Open (kokai) No. 2009-269953 can be used.

Furthermore, into the resist underlayer film composition of the present invention, a basic compound can be blended to improve a storage stability. The basic compound acts as a quencher to an acid to prevent trace of the acid generated from the acid generator from proceeding with a cross-linking reaction.

Specifically, materials described in paragraphs (0086) to (0090) of Japanese Patent Laid-Open (kokai) No. 2007-199653 can be added as such a basic composition.

In the process for forming a resist underlayer film of the present invention, the above resist underlayer film composition is coated onto a substrate to be processed by a method such as spin coating. Adopting the spin coating or the like, allows for obtainment of an excellent filling-up characteristic. After spin coating, baking thereof is conducted in order to evaporate the solvent of the composition, and to promote a cross-linking reaction therein so as to prevent mixing of the composition with a resist upperlayer film, or a resist intermediate film. The baking is conducted at a temperature within a range between 200° C. or more and 600° C. or less, for 10 to 600 seconds or preferably for 10 to 300 seconds. The baking temperature is more preferably between 350° C. or more and 500° C. or less. In consideration of affections on device damage and wafer deformation, the upper limit of heating temperature in a wafer process of lithography is 600° C. or less or preferably 500° C. or less.

As described in SPIE Vol. 469 p. 72 (1984), especially a novolac resin generates a phenoxy radical by being heated, to activate a methylene group of the novolac bond, and thereby the methylene groups are bonded and cross-linked with each other. Since this reaction is a radical reaction, an eliminated molecule does not generate. Therefore, a composition having a high heat resistance does not cause film shrinkage due to cross-linking.

Further, in the process for forming a resist underlayer film of the present invention, the above resist underlayer film composition is coated on a substrate and the resist underlayer film composition is baked in an atmosphere with an oxygen concentration of 0.1% or more and 21% or less to be cured, thereby forming a resist underlayer film.

The resist underlayer film composition of the present invention is baked in such an oxygen atmosphere, thereby enabling to obtain a fully cured resist underlayer film.

Baking atmosphere may be air, and inert gas such as $N_2$, Ar and He may be contained.

Meanwhile, a thickness of this resist underlayer film is appropriately selected, but preferable is 30 to 20,000 nm or particularly 50 to 15,000 nm. After forming the resist underlayer film, in the case of a three-layer process, a silicon-containing resist intermediate film and a resist upperlayer film without silicon can be formed thereon in order.

The resist underlayer film composition of the present invention is extremely useful for a resist underlayer film composition for a multilayer resist process such as a silicon-containing two-layer resist process, a three-layer resist process using a silicon-containing intermediate film and a four-layer resist process using a silicon-containing intermediate film and an organic antireflection film.

A patterning process using the resist underlayer film composition of the present invention is explained below by referring to the three-layer resist process.

The patterning process of the present invention is a patterning process comprising a step of forming a resist underlayer film on a substrate by using the composition for a resist underlayer film described above, a step of forming, over the resist underlayer film, a resist intermediate film by using a silicon-containing composition for a resist intermediate film, a step of forming, over the resist intermediate film, a resist upperlayer film by using a composition for a resist upperlayer film comprised of a photo resist composition thereby forming a multilayer resist film, a step of forming a resist pattern of the resist upperlayer film by developing with a developer after a pattern circuit area of the resist upperlayer film is exposed, a step of etching the resist intermediate film by using a mask of the resist upperlayer film formed with the pattern, a step of etching the resist underlayer film by using a mask of the resist intermediate film at least formed with a pattern, and a step of etching the substrate by using a mask of the resist underlayer film at least formed with a pattern thereby forming a pattern on the substrate.

As mentioned above, it is preferable that etching of the resist underlayer film by using the resist intermediate film as a mask is performed by using an etching gas mainly comprised of an oxygen gas or a hydrogen gas. It is because the silicon-containing intermediate film has an etching resistance to an oxygen gas or a hydrogen gas.

Further, the present invention provides a patterning process for forming a pattern on a substrate by lithography, wherein the process comprises at least:
a step of forming a resist underlayer film on a substrate by using the composition for a resist underlayer film described above, a step of forming, over the resist underlayer film, an inorganic hard mask intermediate film selected from a silicon oxide film, a silicon nitride film, and a silicon oxynitride film, a step of forming, over the inorganic hard mask intermediate film, a resist upperlayer film by using a composition for a resist upperlayer film comprised of a photo resist composition,
a step of forming a resist pattern of the resist upperlayer film by developing with a developer after a pattern circuit area of the resist upperlayer film is exposed, a step of etching the inorganic hard mask intermediate film by using the obtained resist pattern as an etching mask, a step of etching the resist underlayer film by using the obtained inorganic hard mask intermediate film pattern as an etching mask, and
a step of etching the substrate by using the obtained resist underlayer film pattern as an etching mask thereby forming a pattern on the substrate.

As mentioned above, in the case of forming the inorganic hard mask intermediate film on the resist underlayer film, a silicon oxide film, a silicon nitride film and a silicon oxynitride film (SiON film) are formed by CVD method, ALD method or the like. The forming process of the nitride film is described in Japanese Patent Laid-Open (kokai) No. 2002-334869 and WO2004/066377. A film thickness of the inorganic hard mask is 5 to 200 nm or preferably 10 to 100 nm, and in particular, a SiON film which has high effects as an antireflection film is most preferably used among these inorganic hard masks. A substrate temperature in forming the SiON film is raised up to 300° C. to 500° C., so that it is necessary for the resist underlayer film to have a heat resistance to high temperature of 300° C. to 500° C. The resist underlayer film composition used in the patterning process of the present invention has a high resistance to high temperature of 300° C. to 500° C., so that the inorganic hard mask formed by CVD method or ALD method and the resist underlayer film formed by spin coating method can be used in combination.

Further, the present invention can be used suitably for a resist underlayer film of a four-layer resist process using an organic antireflection film. In this case, the present invention can provide a patterning process to form a pattern on a substrate by lithography, wherein the process comprises at least:
a step of forming a resist underlayer film on a substrate by using the composition for a resist underlayer film described above, a step of forming, over the resist underlayer film, an inorganic hard mask intermediate film selected from a silicon oxide film, a silicon nitride film, and a silicon oxynitride film, a step of forming, over the inorganic hard mask intermediate film, an organic anti-reflective film,
a step of forming, over the organic anti-reflective film, a resist upperlayer film by using a composition for a resist upperlayer film comprised of a photo resist composition, a step of forming a resist pattern of the resist upperlayer film by developing with a developer after a pattern circuit area of the resist upperlayer film is exposed, a step of etching the organic anti-reflective film and the inorganic hard mask intermediate film by using the obtained resist pattern as an etching mask, a step of etching the resist underlayer film by using the obtained inorganic hard mask intermediate film pattern as an etching mask, and a step of etching the substrate by using the obtained resist underlayer film pattern as an etching mask to form a pattern on the substrate.

Although it is possible to form a photoresist film as the resist upperlayer film on the resist intermediate film directly, it is also possible to once form an organic antireflective film (BARC) by spin coating on the resist intermediate film and to subsequently form a photoresist film on the organic antireflective film as mentioned above. In the case of adopting a SiON film as the resist intermediate film, it is enabled to restrict reflection by virtue of the two-layer antireflective films, i.e., the SiON film and BARC film, even by a liquid immersion exposure at a higher NA exceeding 1.0. Another merit of the formation of the BARC resides in obtainment of an effect to decrease footing (trailing) of a photoresist pattern compared to a photoresist pattern just above the SiON film.

As the silicon-containing resist intermediate film in the three-layer process, a polysilsesquioxane-based intermediate film is also preferably used. This makes the resist intermediate film to possess an effect as an antireflective film, thereby enabling to suppress reflection. Particularly, when a composition configured to contain many aromatic groups so as to possess a higher resistance against substrate-etching is used as a resist underlayer film for 193 nm exposure, a k value is increased to increase a substrate reflection. Nonetheless, the reflection is restricted by the resist intermediate film, thereby enabling to restrict the substrate reflection down to 0.5% or less. Preferably used as the resist intermediate film having an antireflective effect is a polysilsesquioxane, which has a pendant anthracene for exposure of 248 nm or 157 nm, or a pendant phenyl group or a pendant light-absorbing group having a silicon-silicon bond for 193 nm exposure, and which is cross-linked by an acid or a heat.

In this case, formation of the silicon-containing resist intermediate film by spin coating is more convenient and has a merit of cost than by a CVD method.

The resist upperlayer film in the three-layer resist film may be either a positive type or negative type, and it is possible to use therefor the same one as a typically used photoresist composition. In the case of forming a monolayer of resist upperlayer film by the photoresist composition, spin coating is to be preferably used similarly to the case for forming the resist underlayer film. Prebaking is to be conducted after spin coating of the photoresist composition, preferably at 60 to 180° C. for 10 to 300 seconds. Thereafter, exposure is to be conducted according to a usual manner, followed by post-exposure baking (PEB) and development, to thereby obtain a resist pattern. Although the film thickness of the resist upperlayer film is not particularly limited, the film thickness is to be preferably 30 to 500 nm, particularly 50 to 400 nm.

Further, examples of light for exposure include high energy beams at wavelengths of 300 nm or shorter, specifically excimer lasers at 248 nm, 193 nm, and 157 nm, soft X-rays at 3 to 20 nm, an electron beam, X-rays, and the like.

Next, etching is to be conducted by using the obtained resist pattern as a mask. Etching of a resist intermediate film, particularly an inorganic hard mask, in a three-layer process is to be conducted by using the resist pattern as a mask and by adopting a flon-based gas. Next, etching of the resist underlayer film is to be conducted by using the resist intermediate film pattern, particularly the inorganic hard mask pattern, as a mask and by adopting an oxygen gas or a hydrogen gas.

The subsequent etching of a substrate to be processed can also be conducted according to a usual manner, for example, the manner that etching mainly based on a flon-based gas is conducted for a substrate made of $SiO_2$, SiN or silica-based low dielectric constant insulating film, or etching mainly based on a chlorine-based or bromine-based gas is conducted for a substrate made of p-Si, Al or W. When substrate processing is conducted by etching by a flon-based gas, the silicon-containing intermediate film of the three-layer process is stripped simultaneously with the substrate processing. Only, in the case of etching of a substrate by a chlorine-based gas or a bromine-based gas, stripping of the silicon-containing intermediate film is required to be separately conducted by dry etching stripping by a flon-based gas after substrate processing.

The resist underlayer film of the present invention is characterized in that the film has excellent etching resistance in etching of a substrate to be processed mentioned above.

It is noted that examples of a substrate to be processed embrace a layer to be processed formed on a substrate. Examples of a substrate to be used are not particularly limited and include those made of materials such as Si, α-Si, p-Si, $SiO_2$, SiN, SiON, W, TiN and Al, which are different from those of layers to be processed. Examples of a layer to be processed to be used include various low-k films made of materials such as Si, $SiO_2$, SiON, SiN, p-Si, α-Si, W, W—Si, Al, Cu and Al—Si, and stopper films therefor, which can each typically form into a thickness of 50 to 10,000 nm, particularly 100 to 5,000 nm.

An example of the three-layer resist process will be specifically explained by referring to FIG. 1, as follows.

In the case of the three-layer resist process, the process is configured to form a resist underlayer film 3 on a layer to be processed 2 laminated on a substrate 1, to thereafter form a resist intermediate film 4 thereon, and to form a resist upperlayer film 5 thereon, as shown in FIG. 1(A).

Next, as shown in FIG. 1(B), exposure is conducted for required portions 6 of the resist upperlayer film, followed by PEB and development, to form a resist pattern 5a (FIG. 1(C)). The thus obtained resist pattern 5a is then used as a mask, to etch the resist intermediate film 4 by using a CF-based gas, to thereby form a resist intermediate film pattern 4a (FIG. 1(D)). After removing the resist pattern 5a, the obtained resist intermediate film pattern 4a is used as a mask to etch the resist underlayer film 3 by using an oxygen-plasma, to thereby form a resist underlayer film pattern 3a (FIG. 1(E)). Further, after removing the resist intermediate film pattern 4a, the resist underlayer film pattern 3a is used as a mask to etch the layer to be processed 2, to thereby form a pattern 2a (FIG. 1(F)).

In the case of using an inorganic hard mask intermediate film, the resist intermediate film 4 is the inorganic hard mask intermediate film, and in the case of arranging a BARC, a BARC layer is provided between the resist intermediate film 4 and the resist upperlayer film 5. There is a case that etching of the BARC is to be continuously conducted prior to etching of the resist intermediate film 4, and it is also possible to conduct etching of the BARC only and to subsequently change an etching apparatus to conduct etching of the resist intermediate film 4, for example.

EXAMPLES

Hereinbelow, the present invention will be specifically explained by showing Examples and Comparative Examples; but the present invention is not restricted by these descriptions.

Meanwhile, molecular weights were measured by the method as described below.

Weight-average molecular weight (Mw) and number-average molecular weight (Mn) were measured by a gel permeation chromatography (GPC) as the polystyrene equivalent; and then dispersion degree (Mw/Mn) was obtained.

SYNTHESIS EXAMPLES

Syntheses of a Fullerene Derivative and a Polymer

Synthesis Example 1-1

Synthesis of Fullerene Derivative (F1)

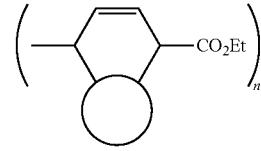

A mixture of 10.0 g of Nanom Mix ST (fullerene mixture of about 60% of $C_{60}$, about 25% of $C_{70}$, and other higher fullerenes; manufactured by Frontier Carbon Corp.) and 40.0 g of ethyl sorbate was heated with stirring under nitrogen atmosphere at 110° C. for 40 hours. An excess ethyl sorbate was removed by distillation under reduced pressure, and then a tetrahydrofurane-soluble fraction was extracted by tetrahydrofurane. The extracted solution was concentrated under reduced pressure; the solid material remained was washed with methanol and then dried to obtain 6.6 g of fullerene derivative (F1) as shown above as a dark brown solid substance. The analysis results of synthesized fullerene derivative (F1) by IR and LC-QTOF are shown below.

IR (KBr): ν=2971, 1734, 1453, 1254, 1179, and 527 cm$^{-1}$

LC-QTOF (Negative/aqueous $AcONH_4$-MeCN): m/z 859 ($C_{68}H_{11}O_2^-$, n=1/$C_{60}$), 999 ($C_{76}H_{23}O_4^-$, n=2/$C_{60}$), 979 ($C_{78}H_{11}O_2^-$, n=1/$C_{70}$), and 1119 ($C_{86}H_{23}O_4^-$, n=2/$C_{70}$)

Synthesis Example 1-2

Synthesis of Fullerene Derivative (F2)

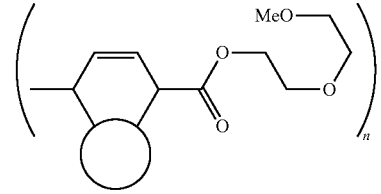

Fullerene derivative (F2) as shown above was obtained as a dark brown solid substance according to the method in Synthesis Example 1-1 except that ethyl sorbate was changed to the corresponding sorbate ester. The analysis results of synthesized fullerene derivative (F2) by IR, $^1$H-NMR, and LC-QTOF are shown below.

IR (KBr): ν=2872, 1734, 1453, 1253, 1175, 1109, and 527 cm$^{-1}$ $^1$H-NMR (600 MHz/CDCl$_3$): δ=1.4-2.3 (3H×n), 3.2-5.5 (13H×n), and 5.9-7.4 (2H×n)

LC-QTOF (Positive/aqueous AcONH$_4$-MeCN): m/z=1380 (C$_{93}$H$_{54}$O$_{12}$+NH$_4^+$, n=3/C$_{60}$) and 1166 (C$_{82}$H$_{36}$O$_8$+NH$_4^+$, n=2/C$_{60}$)

Synthesis Example 1-3

Synthesis of Fullerene Derivative (F3)

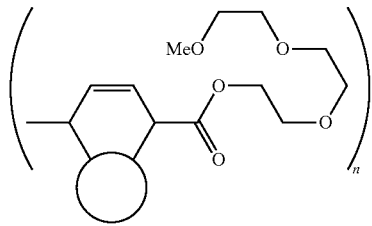

(F3)

A fullerene derivative (F3) as shown above was obtained as a dark brown solid substance according to the method in Synthesis Example 1-1 except that ethyl sorbate was changed to the corresponding sorbate ester. The analysis results of synthesized fullerene derivative (F3) by IR, $^1$H-NMR, and LC-QTOF are shown below.

IR (D-ATR): ν=2877, 1733, 1455, 1244, 1187, 1143, and 733 cm$^{-1}$ $^1$H-NMR (600 MHz/CDCl$_3$): δ=1.4-2.3 (3H×n), 3.2-5.5 (17H×n), and 5.9-7.4 (2H×n)

LC-QTOF (Positive/aqueous AcONH$_4$-MeCN): m/z=1512 (C$_{99}$H$_{66}$O$_{15}$+NH$_4^+$, n=3/C$_{60}$) and 1254 (C$_{86}$H$_{44}$O$_{10}$+NH$_4^+$, n=2/C$_{60}$)

Synthesis Example 1-4

Synthesis of Fullerene Derivative (F4)

Fullerene derivative (F4) was obtained as a dark brown solid substance according to the method described in Tetrahedron, Vol. 52, No. 14, 4983 (1996) except that the used mole ratio of the raw material fullerene was changed to a half of the value described therein. Fullerene derivative (F4) was a mixture mainly comprised of n=2.

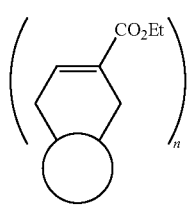

(F4)

Synthesis Example 2

Synthesis of Polymer (R1)

Into a one-liter flask were taken 95 g of 9,9-bis(4-hydroxyphenyl)fluoren, 7 g of 37% aqueous formalin, 5 g of p-toluenesulfonic acid, and 200 g of dioxane; and then the resulting mixture was heated at 100° C. for 24 hours with stirring. After 500 mL of methyl isobutyl ketone was added into the mixture, and then the catalyst and metal impurities were removed by washing with water. The solvent was removed under reduced pressure to obtain polymer (R1).

Molecular weight (Mw) and dispersion degree (Mw/Mn) were obtained by GPC.

Polymer (R1): Mw 9,500 and Mw/Mn 3.90

Preparation of Composition for a Resist Underlayer Film (UDL-1 to UDL-5 and Comparative UDL-1 to UDL-2)

Each of fullerene derivatives (F1) to (F4), polymer (R1), an acid generator shown by AG1, a crosslinking agent shown by CR1, a solvent, and 0.1% by mass solution of FC-4430 (manufactured by Sumitomo 3M Limited) in the solvent were dissolved with the ratio shown in Table 1; and then the resulting solution was filtrated through a 0.1 μm filter made of a fluorinated resin to obtain respective compositions for a resist underlayer film (UDL-1 to UDL-5 and Comparative UDL-1 to UDL-2). AG1 used as the acid generator and CR1 used as the acid generator are shown below.

TABLE 1

| Resist underlayer film composition | Fullerene derivative (parts by mass) | Polymer (parts by mass) | Crosslinking agent (parts by mass) | Acid generator (parts by mass) | Solvent (parts by mass) |
|---|---|---|---|---|---|
| UDL-1 | F1 (10) | R1 (10) | — | — | Cyclohexanone (180) |
| UDL-2 | F2 (10) | R1 (10) | — | — | PGMEA (54)/ Cyclohexanone (126) |
| UDL-3 | F3 (10) | R1 (10) | — | — | PGMEA (54)/ Cyclohexanone (126) |
| UDL-4 | F4 (10) | R1 (10) | — | — | Cyclohexanone (180) |
| UDL-5 | F3 (10) | R1 (10) | CR1 (2) | AG1 (1) | PGMEA (54)/ Cyclohexanone (126) |
| Comparative UDL-1 | None | R1 (20) | — | — | PGMEA (54)/ Cyclohexanone (126) |
| Comparative UDL-2 | None | R1 (20) | CR1 (2) | AG1 (1) | PGMEA (54)/ Cyclohexanone (126) |

PGMEA: Propylene glycol monomethyl ether acetate

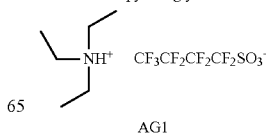

AG1

TABLE 1-continued

| Resist underlayer film composition | Fullerene derivative (parts by mass) | Polymer (parts by mass) | Cross-linking agent (parts by mass) | Acid generator (parts by mass) | Solvent (parts by mass) |
|---|---|---|---|---|---|

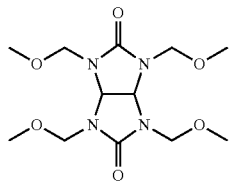

CR1

Measurement of Solvent Resistance

Examples 1 to 5 and Comparative Examples 1 to 2

Each composition for a resist underlayer film (UDL-1 to UDL-5 and Comparative UDL-1 to UDL-2) was applied on a silicon substrate and then baked under the conditions as shown in Table 2; and then film thickness was measured. Thereafter, a PGMEA solution was dispensed thereon, dried by spinning after allowing to stand for 30 seconds, and baked at 100° C. for 60 seconds to evaporate PGMEA; and then film thickness was measured to obtain film thickness difference between before and after the PGMEA treatment.

TABLE 2

| Resist underlayer film composition | Film thickness after coating: a (Å) | Film thickness after PGMEA treatment: b (Å) | b/a × 100 (%) | Temperature | Atmosphere |
|---|---|---|---|---|---|
| Example 1 | UDL-1 | 2410 | 2409 | 100 | 300° C. × 60 sec | nitrogen |
| Example 2 | UDL-2 | 2326 | 2325 | 100 | 300° C. × 60 sec | nitrogen |
| Example 3 | UDL-3 | 2276 | 2276 | 100 | 300° C. × 60 sec | nitrogen |
| Example 4 | UDL-4 | 2386 | 2385 | 100 | 300° C. × 60 sec | nitrogen |
| Example 5 | UDL-5 | 2302 | 2301 | 100 | 300° C. × 60 sec | nitrogen |
| Comparative Example 1 | Comparative UDL-1 | 2440 | 2440 | 100 | 300° C. × 60 sec | nitrogen |
| Comparative Example 2 | Comparative UDL-2 | 2463 | 2461 | 100 | 300° C. × 60 sec | nitrogen |

In any composition for a resist underlayer film of the present invention, a film that was insoluble in the solvent was formed; and thus, a film loss by solvent treatment could be suppressed dramatically, so that solvent resistance (resistance to solvent) could be obtained.

Etching Test by $CF_4/CHF_3$ Gas System

Examples 6 to 10 and Comparative Examples 3 to 4

The resist underlayer film was formed in a manner similar to those of the foregoing, and then the etching test was conducted by $CF_4/CHF_3$ gas system.
Etching Conditions:
Chamber pressure: 40.0 Pa
RF power: 1300 W
$CHF_3$ gas flow: 30 mL/minute
$CF_4$ gas flow: 30 mL/minute
Ar gas flow: 100 mL/minute
Time: 60 seconds By using an etching equipment TE-8500 (manufactured by Tokyo Electron Ltd.), film loss before and after etching was measured. The results are shown in Table 3.

TABLE 3

| Resist underlayer film composition | Film thickness before etching: a (Å) | Film thickness after etching: b (Å) | b/a × 100 (%) |
|---|---|---|---|
| Example 6 | UDL-1 | 2410 | 1501 | 62.3 |
| Example 7 | UDL-2 | 2326 | 1396 | 60.0 |
| Example 8 | UDL-3 | 2276 | 1347 | 59.2 |
| Example 9 | UDL-4 | 2386 | 1343 | 56.3 |
| Example 10 | UDL-5 | 2302 | 1358 | 59.0 |
| Comparative Example 3 | Comparative UDL-1 | 2440 | 1285 | 52.7 |
| Comparative Example 4 | Comparative UDL-2 | 2463 | 1287 | 52.3 |

It was found that the composition for a resist underlayer film of the present invention (UDL-1 to UDL-5) had higher etching resistance as compared with the composition for a resist underlayer film of Comparative Examples (Comparative UDL-1 to UDL-2).

Pattern Etching Test

Examples 11 to 15 and Comparative Examples 5 to 6

Each composition for a resist underlayer film (UDL-1 to UDL-5 and Comparative UDL-1 to UDL-2) was applied onto a 300-mm silicon wafer formed thereon with a $SiO_2$ film having film thickness of 200 nm, and then baked at 300° C. for 60 seconds to form a resist underlayer film having film thickness of 250 nm. Here, baking of the underlayer film was conducted under atmosphere of a nitrogen flow.

Thereafter, a composition for a resist intermediate layer (SOG 1) was applied onto the underlayer film and then baked at 200° C. for 60 seconds to form a resist intermediate film having film thickness of 35 nm, on which an SL resist for ArF (composition for a resist upperlayer film) was applied and then baked at 105° C. for 60 seconds to form a photo resist film having film thickness of 100 nm. Onto the photo resist film was applied a composition for immersion top-coat (TC-1) and then baked at 90° C. for 60 seconds to obtain a top-coat having film thickness of 50 nm.

The composition for a resist intermediate film (SOG 1) was prepared as a propylene glycol ethyl ether containing 2% of the following polymer.

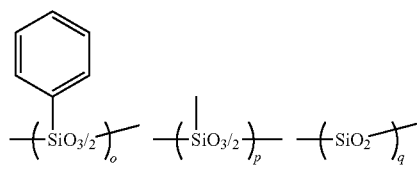

ArF silicon-containing
intermediate film polymer 1
(o = 0.20, p = 0.50, q = 0.30 Mw = 3,400)

The composition for a resist upperlayer film (SL resist for ArF) was prepared as following; a resin shown by ArF monolayer resist polymer 1, acid generator PAG 1, and basic compound amine 1 were dissolved in a solvent containing 0.1% by mass of FC-430 (manufactured by Sumitomo 3M Limited) with the ratio shown in Table 4, and the resulting mixture was filtrated through a 0.1 µm filter made of a fluorinated resin.

TABLE 4

| No. | Polymer (parts by mass) | Acid generator (parts by mass) | Basic compound (parts by mass) | Solvent (parts by mass) |
|---|---|---|---|---|
| SL resist for ArF | ArF monolayer resist polymer 1 (100) | PAG1 (6.6) | amine1 (0.8) | PGMEA (2,500) |

ArF monolayer resist polymer 1, PAG 1, and amine 1, used in the composition, are shown below.

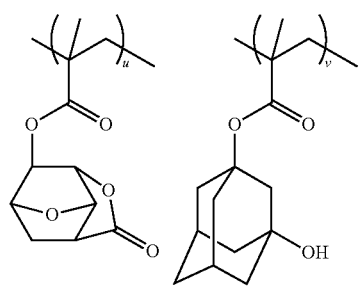

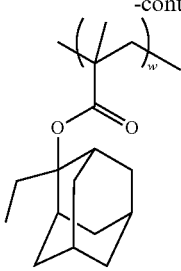

ArF monolayer resist polymer 1
(u = 0.40, v = 0.30, w = 0.30 Mw7,800)

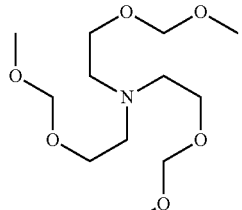

amine 1

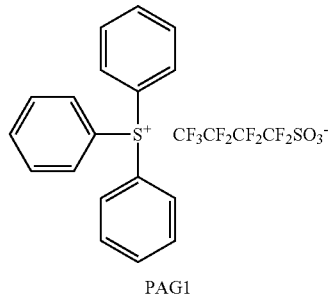

PAG1

The composition for immersion top-coat (TC-1) was prepared by dissolving a top-coat polymer into an organic solvent with the ratio shown in Table 5, followed by filtration of the resulting mixture through a 0.1 µm filter made of a fluorinated resin.

TABLE 5

| No. | Polymer (parts by mass) | Organic solvent (parts by mass) |
|---|---|---|
| TC-1 | Top coat polymer (100) | Diisoamylether (2700) 2-methyl-1-butanol (270) |

The top coat polymer used is shown below.
Top coat polymer:
 Molecular weight (Mw): 8800
 Dispersion degree (Mw/Mn): 1.69

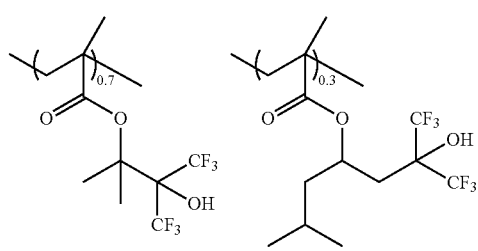

Top coat polymer

Then, exposure was done with an ArF immersion exposure instrument NSR-S610C (manufactured by Nikon Corporation with NA of 1.30, σ of 0.98/0.65, 35-degree dipole s-polarization, and 6% half tone phase shift mask), baking (PEB) was conducted at 100° C. for 60 seconds, and then development was done with an aqueous 2.38% by mass of tetramethyl ammonium hydroxide (TMAH) for 30 seconds to obtain a 1:1 positive line-and-space pattern with 43 nm.

Then, the resist intermediate film was dry etched with an etching instrument Telius (manufactured by Tokyo Electron Ltd.) by using the resist pattern as a mask; the resist underlayer film was etched by using the obtained resist intermediate film pattern as a mask; and the SiO$_2$ film was etched by using the obtained resist underlayer film pattern as a mask. The etching conditions are as shown below.

Conditions for Transfer of the Resist Pattern to the Resist Intermediate Film:
Chamber pressure: 10.0 Pa
RF power: 1500 W
CF$_4$ gas flow: 75 sccm
O$_2$ gas flow:
Time: 15 seconds Conditions for Transfer of the Resist Intermediate Film Pattern to the Resist Underlayer Film:
Chamber pressure: 2.0 Pa
RF power: 500 W
Ar gas flow: 75 sccm
O$_2$ gas flow: 45 sccm
Time: 120 seconds Conditions for Transfer of the Resist Underlayer Film Pattern to the SiO$_2$ Film:
Chamber pressure: 2.0 Pa
RF power: 2200 W
C$_5$F$_{12}$ gas flow: 20 sccm
C$_2$F$_6$ gas flow: 10 sccm
Ar gas flow: 300 sccm
O$_2$: 60 sccm
Time: 90 seconds Pattern cross sections were checked with an electron microscope S-4700 (manufactured by Hitachi, Ltd.), and the results of the profiles compared are shown in Table 6.

ing group, in Examples 11 to 15 did not have a poisoning problem during the upperlayer patterning; and in addition, etching resistance during substrate etching was improved, and pattern wiggling after the substrate transfer etching was depressed, so that pattern transfer to the substrate could be improved. On the other hand, wiggling was caused after the substrate transfer etching in Comparative Examples 5 and 6.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:

1. A composition for a resist underlayer film of a multilayer resist film used in lithography, wherein the composition comprises at least (A) a fullerene derivative having an electron-withdrawing group and that is a reaction product of a substance having a fullerene skeleton with a 1,3-diene compound derivative having an electron-withdrawing group and (B) an organic solvent.

2. The composition for a resist underlayer film according to claim 1, wherein the fullerene derivative contains "n" numbers of a partial structure shown by the following general formula (1):

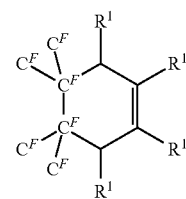

wherein
each R$^1$ independently represents a hydrogen atom, a nitro group, a cyano group, a carboxyl group, a hydroxy

TABLE 6

| | Resist underlayer film composition | Pattern profile after developping | Profile after intermediate film transfer etching | Profile after underlayer film transfer etching | Profile after substrate transfer etching | Wiglling of pattern after substrate transfer etching |
|---|---|---|---|---|---|---|
| Example 11 | UDL-1 | Vertical profile | Vertical profile | Vertical profile | Vertical profile | Non-Exsistence |
| Example 12 | UDL-2 | Vertical profile | Vertical profile | Vertical profile | Vertical profile | Non-Exsistence |
| Example 13 | UDL-3 | Vertical profile | Vertical profile | Vertical profile | Vertical profile | Non-Exsistence |
| Example 14 | UDL-4 | Vertical profile | Vertical profile | Vertical profile | Vertical profile | Non-Exsistence |
| Example 15 | UDL-5 | Vertical profile | Vertical profile | Vertical profile | Vertical profile | Non-Exsistence |
| Comparative Example 5 | Comparative UDL-1 | Vertical profile | Vertical profile | Vertical profile | Taper Profile | Existence |
| Comparative Example 6 | Comparative UDL-2 | Vertical profile | Vertical profile | Vertical profile | Taper Profile | Existence |

The compositions for a resist underlayer film of the present invention containing the fullerene derivative, which is a reaction product of a substance having a fullerene skeleton with a 1,3-diene compound derivative having an electron-withdrawgroup, a sulfo group, or a monovalent organic group having 1 to 20 carbon atoms, and that may contain any one or more of a cyano group, a carboxyl group, a hydroxy group, a nitro group, a sulfo group, a carbonyl group, an ether group, an ester group, a sulfone group, and a halogen atom, wherein one or more $R^1$ is an electron-withdrawing group and two or more $R^1$ may be bonded with each other to form a ring;

$C^F$ represents a carbon atom that composes a fullerene skeleton of the fullerene derivative; and reference character "n" represents an integer of 1 to 30.

3. The composition for a resist underlayer film according to claim 1, wherein the electron-withdrawing group is any of a cyano group, a carboxyl group, a nitro group, a sulfo group, an acyl group, an alkoxy carbonyl group, an alkane sulfonyl group, and a trifluoromethyl group.

4. The composition for a resist underlayer film according to claim 2, wherein the electron-withdrawing group is any of a cyano group, a carboxyl group, a nitro group, a sulfo group, an acyl group, an alkoxy carbonyl group, an alkane sulfonyl group, and a trifluoromethyl group.

5. The composition for a resist underlayer film according to claim 1, wherein the 1,3-diene compound derivative having an electron-withdrawing group is a sorbate ester.

6. The composition for a resist underlayer film according to claim 2, wherein the 1,3-diene compound derivative having an electron-withdrawing group is a sorbate ester.

7. The composition for a resist underlayer film according to claim 3, wherein the 1,3-diene compound derivative having an electron-withdrawing group is a sorbate ester.

8. The composition for a resist underlayer film according to claim 4, wherein the 1,3-diene compound derivative having an electron-withdrawing group is a sorbate ester.

9. The composition for a resist underlayer film according claim 1, wherein the fullerene derivative contains "n" numbers of a partial structure shown by the following general formula (1a):

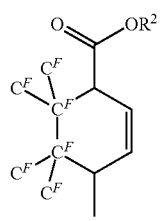

(1a)

wherein $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

10. The composition for a resist underlayer film according claim 2, wherein the fullerene derivative contains "n" numbers of a partial structure shown by the following general formula (1a):

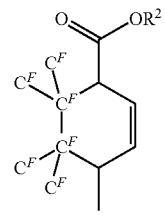

(1a)

wherein $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

11. The composition for a resist underlayer film according claim 3, wherein the fullerene derivative contains "n" numbers of a partial structure shown by the following general formula (1a):

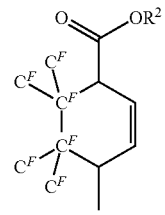

(1a)

wherein $R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

12. The composition for a resist underlayer film according claim 4, wherein the fullerene derivative contains "n" numbers of a partial structure shown by the following general formula (1a):

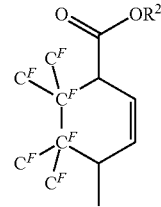

(1a)

wherein

R² represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

13. The composition for a resist underlayer film according claim 5, wherein the fullerene derivative contains "n" numbers of a partial structure shown by the following general formula (1a):

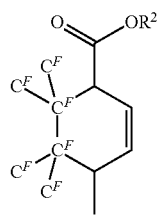

(1a)

wherein

R² represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

14. The composition for a resist underlayer film according claim 6, wherein the fullerene derivative contains "n" numbers of a partial structure shown by the following general formula (1a):

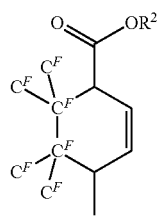

(1a)

wherein

R² represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

15. The composition for a resist underlayer film according claim 7, wherein the fullerene derivative contains "n" numbers of a partial structure shown by the following general formula (1a):

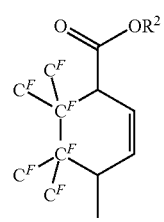

(1a)

wherein

R² represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

16. The composition for a resist underlayer film according claim 8, wherein the fullerene derivative contains "n" numbers of a partial structure shown by the following general formula (1a):

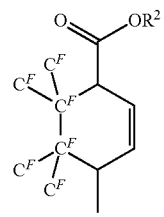

(1a)

wherein

R² represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;

$C^F$ represents a carbon atom that composes a fullerene skeleton of the fullerene derivative; and reference character "n" represents an integer of 1 to 30.

17. The composition for a resist underlayer film according to claim 1, further comprising (C) a resin having an aromatic ring.

18. The composition for a resist underlayer film according to claim 16, further comprising (C) a resin having an aromatic ring.

19. The composition for a resist underlayer film according to claim 17, wherein (C) the resin having an aromatic ring contains a naphthalene ring.

20. The composition for a resist underlayer film according to claim 18, wherein (C) the resin having an aromatic ring contains a naphthalene ring.

21. The composition for a resist underlayer film according to claim 17, wherein (C) the resin having an aromatic ring contains at least a compound (C1) that is obtained by polycondensation of a compound shown by the following general formula (2) and a compound shown by the following general formula (3) under an acidic condition:

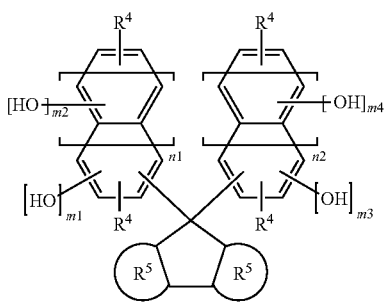

(2)

A-CHO (3)

wherein
each $R^4$ independently represents a hydrogen atom or a hydrocarbon group having 6 to 20 carbon atoms;
each $R^5$ independently represents a benzene ring or a naphthalene ring;
$1 \leq m1+m2 \leq 2$ and $1 \leq m3+m4 \leq 2$;
n1 and n2 are 0 or 1, respectively; and
A represents any of a hydrogen atom, a linear, a branched, or a cyclic saturated or unsaturated hydrocarbon group having 1 to 20 carbon atoms, and an aromatic hydrocarbon group having 6 to 20 carbon atoms, wherein A may contain an ether group, a nitro group, a hydroxy group, or a chlorine group.

22. The composition for a resist underlayer film according to claim 20, wherein (C) the resin having an aromatic ring contains at least a compound (C1) that is obtained by polycondensation of a compound shown by the following general formula (2) and a compound shown by the following general formula (3) under an acidic condition:

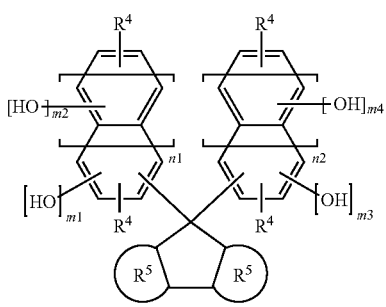

(2)

A-CHO (3)

wherein
each $R^4$ independently represents a hydrogen atom or a hydrocarbon group having 6 to 20 carbon atoms;
each $R^5$ independently represents a benzene ring or a naphthalene ring;
$1 \leq m1+m2 \leq 2$ and $1 \leq m3+m4 \leq 2$;
n1 and n2 are 0 or 1, respectively; and
A represents any of a hydrogen atom, a linear, a branched, or a cyclic saturated or unsaturated hydrocarbon group having 1 to 20 carbon atoms, and an aromatic hydrocarbon group having 6 to 20 carbon atoms, wherein A may contain an ether group, a nitro group, a hydroxy group, or a chlorine group.

23. The composition for a resist underlayer film according to claim 1, further comprising at least one selected from the group consisting of (D) a phenolic-hydroxy group containing compound, (E) an acid generator, (F) a crosslinking agent, and (G) a surfactant.

24. The composition for a resist underlayer film according to claim 22, further comprising at least one selected from the group consisting of (D) a phenolic-hydroxy group containing compound, (E) an acid generator, (F) a crosslinking agent, and (G) a surfactant.

25. A process for forming a resist underlayer film of a multilayer resist film used in lithography, comprising applying the composition for a resist underlayer film according to claim 1 onto a substrate, and then curing the composition for a resist underlayer film by heat-treatment at a temperature of 200° C. or higher and 600° C. or lower and a time of 10 to 600 seconds to form a resist underlayer film.

26. A process for forming a resist underlayer film of a multilayer resist film used in lithography, comprising applying the composition for a resist underlayer film according to claim 1 onto a substrate, and then curing the composition for a resist underlayer film by baking under an atmosphere of oxygen concentration of 0.1% or higher and 21% or lower to form a resist underlayer film.

27. A patterning process for forming a pattern on a substrate by lithography, wherein the process comprises at least:
forming a resist underlayer film on a substrate by using the composition for a resist underlayer film according to claim 1,
forming, over the resist underlayer film, a resist intermediate film by using a silicon-containing composition for a resist intermediate film,
forming, over the resist intermediate film, a resist upperlayer film by using a composition for a resist upperlayer film comprised of a photo resist composition thereby forming a multilayer resist film,
forming a resist pattern of the resist upperlayer film by developing with a developer after a pattern circuit area of the resist upperlayer film is exposed,
etching the resist intermediate film by using a mask of the resist upperlayer film formed with the pattern,
etching the resist underlayer film by using a mask of the resist intermediate film at least formed with a pattern, and
etching the substrate by using a mask of the resist underlayer film at least formed with a pattern thereby forming a pattern on the substrate.

28. The patterning process according to claim 27, wherein etching of the resist underlayer film by using a mask of the resist intermediate film is carried out in an etching gas mainly comprised of an oxygen gas or a hydrogen gas.

29. A patterning process for forming a pattern on a substrate by lithography, wherein the process comprises at least:
forming a resist underlayer film on a substrate by using the composition for a resist underlayer film according to claim 1,
forming, over the resist underlayer film, an inorganic hard mask intermediate film selected from a silicon oxide film, a silicon nitride film, and a silicon oxynitride film,
forming, over the inorganic hard mask intermediate film, a resist upperlayer film by using a composition for a resist upperlayer film comprised of a photo resist composition,
forming a resist pattern of the resist upperlayer film by developing with a developer after a pattern circuit area of the resist upperlayer film is exposed,
etching the inorganic hard mask intermediate film by using the obtained resist pattern as an etching mask,
etching the resist underlayer film by using the obtained inorganic hard mask intermediate film pattern as an etching mask, and
etching the substrate by using the obtained resist underlayer film pattern as an etching mask thereby forming a pattern on the substrate.

30. A patterning process for forming a pattern on a substrate by lithography, wherein the process comprises at least:
forming a resist underlayer film on a substrate by using the composition for a resist underlayer film according to claim 1,
forming, over the resist underlayer film, an inorganic hard mask intermediate film selected from a silicon oxide film, a silicon nitride film, and a silicon oxynitride film,
forming, over the inorganic hard mask intermediate film, an organic anti-reflective film,
forming, over the organic anti-reflective film, a resist upperlayer film by using a composition for a resist upperlayer film comprised of a photo resist composition,
forming a resist pattern of the resist upperlayer film by developing with a developer after a pattern circuit area of the resist upperlayer film is exposed,
etching the organic anti-reflective film and the inorganic hard mask intermediate film by using the obtained resist pattern as an etching mask,
etching the resist underlayer film by using the obtained inorganic hard mask intermediate film pattern as an etching mask, and
etching the substrate by using the obtained resist underlayer film pattern as an etching mask to form a pattern on the substrate.

31. The patterning process according to claim 29, wherein the inorganic hard mask intermediate film is formed by a CVD method or an ALD method.

32. The patterning process according to claim 30, wherein the inorganic hard mask intermediate film is formed by a CVD method or an ALD method.

33. A fullerene derivative having "n" numbers of a partial structure shown by the following general formula (1a):

wherein
$R^2$ represents any of a linear, a branched, or a cyclic alkyl group having 1 to 19 carbon atoms, an aryl group having 6 to 15 carbon atoms, a hetero aryl group having 4 to 15 carbon atoms, and an aralkyl group having 7 to 19 carbon atoms, wherein the group may contain any one or more of a carbonyl group, an ether group, an ester group, a cyano group, a carboxyl group, a hydroxy group, and a halogen atom;
$C^F$ represents a carbon atom that composes a fullerene skeleton of the fullerene derivative; and
reference character "n" represents an integer of 2 to 10.

* * * * *